United States Patent
Berde et al.

(10) Patent No.: US 6,238,702 B1
(45) Date of Patent: *May 29, 2001

(54) HIGH LOAD FORMULATIONS AND METHODS FOR PROVIDING PROLONGED LOCAL ANESTHESIA

(75) Inventors: Charles B. Berde, Brookline; Robert S. Langer, Newton, both of MA (US); Joanne Curley, San Jose, CA (US); Jenny Castillo, Philadelphia, PA (US)

(73) Assignee: Children's Medical Center Corp., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/352,511

(22) Filed: Jul. 12, 1999

Related U.S. Application Data

(63) Continuation of application No. 08/714,782, filed on Sep. 16, 1996, now Pat. No. 5,922,340, which is a continuation-in-part of application No. 08/432,402, filed on May 1, 1995, now Pat. No. 5,700,485, which is a continuation-in-part of application No. 08/119,958, filed on Sep. 10, 1993, now Pat. No. 5,618,563, which is a continuation-in-part of application No. 07/943,287, filed on Sep. 10, 1992, now abandoned.

(51) Int. Cl.⁷ ................................................. A61K 9/14
(52) U.S. Cl. ....................... 424/489; 424/400; 424/422; 424/426
(58) Field of Search .................... 424/489, 426, 424/464, 484, 486, 488, 436, 400, 422

(56) References Cited

U.S. PATENT DOCUMENTS

| | | | |
|---|---|---|---|
| 2,174,796 | 10/1939 | Luzzi | 32/34 |
| 2,835,628 | 5/1958 | Saffir | 167/84 |
| 3,185,625 | 5/1965 | Brown | 167/82 |
| 3,337,400 | 8/1967 | Smith | 167/52 |
| 3,507,952 | 4/1970 | Rednick et al. | 424/22 |
| 3,535,419 | 10/1970 | Siegrist et al. | 424/22 |

(List continued on next page.)

FOREIGN PATENT DOCUMENTS

| | | | |
|---|---|---|---|
| 1143289 | 3/1983 | (CA) | A61K/9/50 |
| 2930248 | 2/1981 | (DE) | B01J/13/02 |
| 0195906 | 2/1986 | (EP) | A61K/31/71 |
| 0244118 | 11/1987 | (EP) | A61K/9/10 |

(List continued on next page.)

OTHER PUBLICATIONS

Berde, C.B., et al., "Sustained Release of Dibucaine from a Biodegradable Polymer Matrix: A Potential Method for Prolonged Neural Blockade", Abstracts of Scientific Papers, 1990 Annual Meeting, Amer. Soc. Anesthesiologists, 73:A776 (Sep. 1990).

Edelman, Elazer R, et al., "Optimization of release from magnetically controlled polymeric drug release devices", *Biomaterials*, 14(8):621–626 (1993).

Masters, et al., Abstract No. 94.3, "Prolonged Sciatic Nerve Blockade Using Sustained Release of Veratridine From a Biodegradable Polymer Matrix", *Soc. Neurosci. Abstr.*, 18:200 (1992).

(List continued on next page.)

Primary Examiner—James M. Spear
Assistant Examiner—Rachel M Bennett
(74) Attorney, Agent, or Firm—Davidson, Davidson & Kappel, LLC

(57) ABSTRACT

A formulation for inducing sustained local anesthesia in a patient comprising a substrate comprising a high load of local anesthetic by weight and an effective amount of a biocompatible, controlled release material to obtain a. reversible nerve blockade or anesthesia effect when implanted or injected in a patient, and a non-toxic glucocorticosteroid agent effective to prolong the duration of the local anesthesia for a time period longer than that obtainable from the substrate without the glucocorticosteroid agent.

38 Claims, 6 Drawing Sheets

U.S. PATENT DOCUMENTS

| | | | |
|---|---|---|---|
| 3,736,646 | 6/1973 | Schmitt et al. | 29/458 |
| 3,755,558 | 8/1973 | Scribner | 424/47 |
| 3,773,919 | 11/1973 | Boswell et al. | 424/19 |
| 3,844,285 | 10/1974 | Laby | 128/260 |
| 3,887,699 | 6/1975 | Yolles | 424/19 |
| 3,943,063 | 3/1976 | Morishita et al. | 252/316 |
| 3,972,995 | 8/1976 | Tsuk et al. | 424/28 |
| 3,972,999 | 8/1976 | Tsuk | 424/78 |
| 3,976,071 | 8/1976 | Sadek | 128/260 |
| 3,991,766 | 11/1976 | Schmitt et al. | 128/335.5 |
| 4,001,388 | 1/1977 | Shell | 424/14 |
| 4,011,312 | 3/1977 | Reuter et al. | 424/78 |
| 4,034,758 | 7/1977 | Theeuwes | 128/260 |
| 4,039,653 | 8/1977 | DeFoney et al. | 424/19 |
| 4,070,347 | 1/1978 | Schmitt | 260/77.5 D |
| 4,076,798 | 2/1978 | Casey et al. | 424/22 |
| 4,089,800 | 5/1978 | Temple | 252/316 |
| 4,093,709 | 6/1978 | Choi et al. | 424/19 |
| 4,118,470 | 10/1978 | Casey et al. | 424/19 |
| 4,131,648 | 12/1978 | Choi et al. | 424/22 |
| 4,138,344 | 2/1979 | Choi et al. | 252/1 |
| 4,144,317 | 3/1979 | Higuchi et al. | 424/21 |
| 4,164,560 | 8/1979 | Folkman et al. | 424/22 |
| 4,166,107 | 8/1979 | Miller et al. | 424/19 |
| 4,166,800 | 9/1979 | Fong | 252/316 |
| 4,175,326 | 11/1979 | Goodson | 433/80 |
| 4,226,848 | 10/1980 | Nagai et al. | 424/19 |
| 4,250,163 | 2/1981 | Nagai et al. | 424/14 |
| 4,276,880 | 7/1981 | Malmin | 128/221 |
| 4,293,539 | 10/1981 | Ludwig et al. | 424/19 |
| 4,321,038 | 3/1982 | Porteous | 433/136 |
| 4,331,728 * | 5/1982 | Theeuwes | 428/215 |
| 4,369,172 | 1/1983 | Schor et al. | 424/19 |
| 4,384,975 | 5/1983 | Fong | 427/213.36 |
| 4,389,330 | 6/1983 | Tice et al. | 427/213.36 |
| 4,404,183 | 9/1983 | Kawata et al. | 424/19 |
| 4,419,340 | 12/1983 | Yolles | 424/19 |
| 4,434,153 | 2/1984 | Urquhart et al. | 424/22 |
| 4,479,911 | 10/1984 | Fong | 264/4.6 |
| 4,530,840 | 7/1985 | Tice et al. | 514/179 |
| 4,542,025 | 9/1985 | Tice et al. | 424/78 |
| 4,557,925 | 12/1985 | Lindahl et al. | 424/19 |
| 4,568,535 | 2/1986 | Loesche | 424/19 |
| 4,568,536 | 2/1986 | Kronenthal et al. | 424/22 |
| 4,569,837 | 2/1986 | Suzuki et al. | 424/28 |
| 4,585,651 | 4/1986 | Beck et al. | 424/88 |
| 4,597,960 | 7/1986 | Cohen | 424/28 |
| 4,622,219 | 11/1986 | Haynes | 424/38 |
| 4,622,244 | 11/1986 | Lapka et al. | 427/213.32 |
| 4,623,588 | 11/1986 | Nuwayser et al. | 428/402.24 |
| 4,650,665 | 3/1987 | Kronenthal et al. | 424/435 |
| 4,652,441 | 3/1987 | Okada et al. | 424/19 |
| 4,685,883 | 8/1987 | Jernberg | 433/136 |
| 4,713,244 | 12/1987 | Bawa et al. | 424/429 |
| 4,716,203 | 12/1987 | Casey et al. | 525/408 |
| 4,725,442 | 2/1988 | Haynes | 424/490 |
| 4,735,945 | 4/1988 | Sakamoto et al. | 514/279 |
| 4,756,907 | 7/1988 | Beck et al. | 424/85 |
| 4,757,128 | 7/1988 | Domb et al. | 528/271 |
| 4,767,628 | 8/1988 | Hutchinson | 424/426 |
| 4,780,320 | 10/1988 | Baker | 424/493 |
| 4,789,726 | 12/1988 | Hutchinson | 528/354 |
| 4,801,739 | 1/1989 | Franz et al. | 560/185 |
| 4,861,627 | 8/1989 | Mathiowitz et al. | 427/213.31 |
| 4,874,612 | 10/1989 | Deasy | 424/425 |
| 4,882,168 | 11/1989 | Casey et al. | 424/468 |
| 4,883,666 | 11/1989 | Sabel et al. | 424/422 |
| 4,888,176 | 12/1989 | Langer et al. | 424/426 |
| 4,891,225 | 1/1990 | Langer et al. | 424/428 |
| 4,892,736 | 1/1990 | Goodson | 424/435 |
| 4,906,474 | 3/1990 | Langer et al. | 424/428 |
| 4,919,939 | 4/1990 | Baker | 424/493 |
| 4,933,182 | 6/1990 | Higashi et al. | 424/425 |
| 5,000,886 | 3/1991 | Lawter et al. | 264/4.3 |
| 5,004,602 | 4/1991 | Hutchison | 424/78 |
| 5,007,790 | 4/1991 | Shell | 424/451 |
| 5,013,553 | 5/1991 | Southard et al. | 424/426 |
| 5,019,379 | 5/1991 | Domb et al. | 424/78 |
| 5,019,400 | 5/1991 | Gombotz et al. | 424/497 |
| 5,032,384 | 7/1991 | Yeh et al. | 424/49 |
| 5,061,492 * | 10/1991 | Okada et al. | 424/423 |
| 5,075,109 | 12/1991 | Tice et al. | 424/88 |
| 5,084,267 | 1/1992 | Damani | 424/426 |
| 5,100,669 | 3/1992 | Hyon et al. | 424/426 |
| 5,114,718 | 5/1992 | Damani | 424/422 |
| 5,122,367 | 6/1992 | Ron et al. | 424/80 |
| 5,143,661 | 9/1992 | Lawler et al. | 264/4.3 |
| 5,188,837 | 2/1993 | Domb | 424/450 |
| 5,198,220 | 3/1993 | Damani | 424/426 |
| 5,222,529 | 6/1993 | Zoltan | 141/4 |
| 5,225,441 | 7/1993 | Vogel et al. | 514/557 |
| 5,227,165 | 7/1993 | Domb et al. | 424/450 |
| 5,236,355 | 8/1993 | Brizzolara et al. | 433/80 |
| 5,244,678 * | 9/1993 | Legros et al. | 424/450 |
| 5,252,701 | 10/1993 | Jarrett et al. | 528/354 |
| 5,264,207 | 11/1993 | Bommelaer et al. | 424/69 |
| 5,272,139 | 12/1993 | Cary, Jr. | 514/171 |
| 5,330,452 | 7/1994 | Zook | 604/307 |
| 5,401,507 | 3/1995 | Lewis | 424/426 |
| 5,407,609 | 4/1995 | Tice et al. | 264/46 |
| 5,492,901 | 2/1996 | Fabunan | 514/171 |
| 5,540,912 | 7/1996 | Roorda et al. | 424/422 |
| 5,543,156 | 8/1996 | Roorda et al. | 424/484 |
| 5,618,563 | 4/1997 | Berde et al. | 424/501 |
| 5,650,173 | 7/1997 | Ramstack et al. | 424/489 |
| 5,654,008 | 8/1997 | Herbert et al. | 424/489 |
| 5,700,485 | 12/1997 | Berde et al. | 424/501 |
| 5,747,060 | 5/1998 | Sackler et al. | 424/426 |
| 5,922,340 * | 7/1999 | Berde et al. | 424/426 |
| 5,942,241 | 8/1999 | Chasin et al. | 424/426 |
| 6,046,187 | 4/2000 | Berde et al. | 514/180 |

FOREIGN PATENT DOCUMENTS

| | | | |
|---|---|---|---|
| 0430474 | 6/1991 | (EP) | A61K/9/70 |
| 2592791 * | 7/1987 | (FR) . | |
| 2034182 | 6/1980 | (GB) | A61K/9/00 |
| 9117772 | 11/1991 | (WO) | A61K/47/30 |
| 9207555 | 5/1992 | (WO) | A61K/9/22 |
| 9215286 | 9/1992 | (WO) | A61K/9/22 |
| WO9215286 | 9/1992 | (WO) | A61K/9/22 |
| WO9320138 | 10/1993 | (WO) . | |
| WO9405265 | 3/1994 | (WO) | A61K/9/20 |
| 9513799 | 5/1995 | (WO) | A61K/9/50 |
| WO9641616 | 12/1996 | (WO) | A61K/9/14 |

OTHER PUBLICATIONS

Fong, Jones W., et al., "Evaluation of biodegradable microspheres prepared by a solvent evaporation process using sodium oleate as emulsifier", *Journal of Controlled Release*, 3:119–130 (1986).

Fong, J.W., "Microencapsulation by Solvent Evaporation and Organic Phase Separation Processes," pp. 81–108, chapter 5 from *Controlled Release Systems: Fabrication Technology*, Ed. Dean Hsieh, Ph.D., vol. 1.

Masters, David B., et al. , "Prolonged Regional Nerve Blockade by Controlled Release of Local Anesthesia from a Biodegradable Polymer Matrix", *Anesthesiology*, 79:340–346 (1993).

Miyazaki, S., et al., "External control of drug release: controlled release of insulin from a hydrophilic polymer implant by ultrasound irradiation in diabetic rats", *J. Pharm. Pharmacol.,* 40:716–717 (1988).

Sato, T., et al., "Porous Biodegradable Microspheres for Controlled Drug Delivery. I. Assessment of Processing Conditions and Solvent Removal Techniques", *Pharmaceutical Research,* 5:21–30 (1988).

Schneider, Markus, M.D., et al., "A Preferential Inhibition of Impulses in C–fibers of the Rabbit Vagus Nerve by Veratridine, an Activator of Sodium Channels", *Anesthesiology,* 74:270–280 (1991).

Tice, Thomas R., et al., "Preparation of Injectable Controlled–Release Microcapsules by a Solvent–Evaporation Process", Journal of Controlled Release, 2:343–352 (1985).

Wakiyama, Naoki, et al., "Preparation and Evaluation in Vitro and in Vivo of Polylactic Acid Microspheres containing Dibucaine", *Chem. Pharm. Bull,* 30:3719–3727 (1982).

Duncan, et al., "Treatment of Upper Extremity Reflex Sympathetic Dystrophy with Joint Stiffness Using Sympatholytic Bier Blocks and Manipulation" *Orthopedics* 11(6), pp. 883–886, (1988).

Flanagan, et al., "Intra–articular injection for pain relief in patients awaiting hip replacement", *Ann. Royal Coll. Surg. Eng.,* vol. 70, pp 156–157 (1988).

Glasser, et al., "The perioperative use of corticosteroids and bupivacaine in the management of lumbar disc disease", *J. Neurosurg.,* vol. 78, pp. 383–387, (1993).

Guttu, et al., "Delayed Healing of Muscle After Injection of Bupivacaine and Steroid", *Annals of Dentistry,* 49:5–8, (1990).

Hall, et al., "Acute effects of intravenous glucocorticoid on cat spinal motor neuron electrical properties", *Brain Research,* vol. 240, pp. 186–190, (1982).

Sandrock and Warfield, "Epidural Steroids and Facet Injections", Ch. 29 *Principles and Practice of Pain Management,* Warfield, C.A., editor (McGraw–Hill, Inc. 1993).

Waldman, et al., "The Relief of Body Wall Pain Secondary to Malignant Hepatic Metastases by Intercostal Nerve Block with Bupivacaine and Methylprednisolone", *J. Pain Symptom Management,* 3(1), 39–43 (1988), (see in particular p. 42, col. 2).

Bonica, John J. and F. Peter Buckley, "Regional Analgesia with Local Anesthetics", *The Management of Pain II;* pp. 1883–1966, (1990), Lea & Febiger (Eds.) Second Edition.

Lewis, D.H., et al., "The Use of In Vitro Release Methods to Guide the Development of Controlled–Release Formulations", 9th International Symposium on Controlled Release of Bioactive Maerials, Sponsored by Controlled Release Society, Inc., pp. 61–64.

Masters, D.B., et al., Meeting for the American Society of Anesthesiologists, vol. 75:A680, (1991).

Devor, et al., 1983, "Axoplasmic Transport Block Reduces Ectopic Impulse Generation in Injured Peripheral Nerves", pp. 73–85.

Schnebel, et al., "The Use of Oral Colchicine for Low–Back Pain", 1987, pp. 354–357.

March, et al., "Biodegradable Microspheres Containing a Colchicine Analogue Inhibit DNA Synthesis in Vascular Smooth Muscle Cells", 1994, pp. 1929–1933.

CA 125:104914,. Joanne Curley, et al., "Prolonged regional nerve blockade: Injectable biodegradable bupivacaine/polyester microspheres".

Jean–Marc Malinovsky, et al., "Motor and Blood Pressures Effects of Epidural Sustained–Release Bupivacaine from Polymer Microspheres: A Dose–Response Study in Rabbits", Anesth. Analg 1995, 81:519–24.

L.S. Goodman, et al., "The Pharmacological Basis of Therapeutics", Fourth Edition, 1970, The MacMillan Co., p. 372.

Vol. IA "Drug Information for the Health Care Professional", USP DI, 1989, Ninth Edition, Anesthetics (Mucosal–Local), pp. 183–184; 196–197; 201–203.

Setterstrom, Tice, Lewis and Meyers, "Controlled Release of Antibiotics from Biodegradable Microcapsules fro Wound Infection Control", U.S. Army Institute of Dental Research, (1982), 12 pages.

Abstract: Archer DR, et al. "Changes in slow axonal transport of tubulin induced by local application of colchicine to rabbit vagus nerve", Acta Physiol Scand Jan. 1994 150(1):57–65.

Abstract: Le Corre, et al., "Spinal controlled delivery of bupivacaine from DL–lactic acid oligomer microspheres", J. Pharm Sci Jan. 1995 84(I) 75–78.

Abstract: Gradus–Pizlo, et al., "Local delivery of biodegradable microparticles containing colchicine or a . . . ", J.Am-.Coll. Cardiol. Nov. 1995 26(6) 1549–57.

Abstract: Penickova V., et al., "Vinblastin iontophoresis in treating intractable pain", Aota Univ Palacki Olomuc Fac Med 1990 128:37–47.

Abstract: Kantner, et al., Regulatory mechanism for substance P in the dorsal horn during a nociceptive stimulus; axoplasmic transport vs. electrical activity., Brain Res., Oct. 22, 1986 385(2):282–90.

Abstract: Yarnamoto, et al., "Effects of colchicine applied to the colchicine applied . . . constriction", Pain, Nov. 1993, 55(2):227–33.

Jaffe, Howard, "Microencapsulation Process", copy of government–owned invention description, serial No. 943–940, filed Aug. 17, 1978, U.S. Department of Agriculture, Hyansville, MD, 11 pages.

Algire, Glenn H., et al., "Vascular Reactions of Normal and Malignant Tissues In Vivo. VI. The Role of Hypotension in the Action of Components of Podophyllin on Transplanted Sarcomas", *Journal of the American Cancer institute,* vol. 14, No. 4, Feb. 1954, pp. 879–893.

Baguley, Bruce C., et al., "Inhibition of Growth of Colon 38 Adenocarcinoma by Vinblastine and Colchicine: Evidence for a Vascular Mechanism", *Eur.J. Cancer,* vol. 27, No. 4, pp. 482–487 (1991).

Beck, Lee R., et al., "Poly(DL–Lactide–co–glycolide)/Norethisterone Microcapsules: an Injectable Biodegradable Contraceptive", *Biology of Reproduction,* vol. 28, pp. 186–195 (1983).

Bissery, M.C., et al., "A Study of Process Parameters in the Making of Microspheres by the Solvent Evaporation Procedure", EXPO–Congr. Int. Technol. Pharm., 3rd, pp. 233–239 (1983).

Bodmeier, R., et al., "Solvent selection in the preparation of poly(DL–lactide) microspheres prepared by the solvent evaporation method", *International Journal of Pharmaceutics,* vol. 43, pp. 179–186, (1988).

Bodmeier, R., et al., "Polylactic acid microspheres containing quinidine base and quinidine sulphate prepared by the solvent evaporation technique. II. Some process parameters influencing the preparation and properties of microspheres", *J. Microencapsulation,* vol. 4, No. 4, pp. 289–297 (1987).

Hill, S.A., et al., "Vinca Alkaloids: Anti–vascular Effects in a Murine Tumour", *Euro. J. Cancer*, vol. 29A, No. 9, pp. 1320–1324 (1993).

Jalil, R., et al., "Microencapsulation using poly(L–lactic acid) I: Microcapsule properties affected by the preparative technique", *J. Microencapsul.*, vol. 6, No. 4, pp. 473–484 (Oct.–Dec.) (1989).

Lin, Shan–Yang, et al., " Insulin Controlled–release Microcapsules to Prolong the Hypoglycemic Effect in Diabetic Rats", *Biomat. Art. Cells, Art. Org.*, vol. 16, No. 4, pp. 815–828 (1988).

Lin, Shan–Yang, et al., "Microencapsulation and controlled release of insulin from polylactic acid microcapsules", *Biomat. Med. Dev., Art. Org.*, vol. 13, Nos. 3&4, pp. 187–201 (1985–86).

Mathiowitz, E., et al., "Polyanhydride Microspheres as Drug Carriers. II. Microencapsulation by Solvent Removal", *Journal of Applied Polymer Science*, vol. 35, pp. 755–774 (1988).

Splenlehauer, G., et al., "In vitro and in vivo degradation of poly(D,L lactide/glycolide) type microspheres made by solvent evaporation method", *Biomaterials*, vol. 10, pp. 557–563 (Oct. 1989).

Thies, Curt, "Microcapsules as Drug Devices Systems", *Crit. Rev. Biomed. Eng.*, vol. 8, Issue 4, pp. 335–383 (1982).

Windholz, M., et al. *The Merck Index*, 10th Edition, p. 37, Abstract #225 (1983).

Thomas R. Tice, et al. Biodegradation of Microcapsules and Biomedical Devices Prepared with Resorbable Polyesters, Southern Research Institute, University of Alabama (pp. 21–23).

William T. Buchanan, et al. Systemic Effects of epinephrine–impregnated retraction cord in fixed partial denture prosthodontics, JADA, vol. 104, Apr. 1982.

David B. Masters, et al., Sustained Local Anesthetic Release from Bioerodible Polymer Matrices: A Potential Method for Prolonged Regional Anesthesia, Pharmaceutical Research, vol. 10, No. 10, pp. 1527–1532, 1993.

N.H. Shah, et al., A biodegradable injectable implant for delivering micro and macromolecules using poly (lactic–co–glycolic) acid (PLGA) copolymers, Journal of Controlled Release, 27 (1993) 139–147.

D.L. Williams, Microencapsulated Local Anesthetics, Proc. Int Symp. Rel Bioact Mater, 11:69–070 (1984).

Journal of Dental Research, IADR Abstract Papers, vol. 61, Papers 860 and 861, Mar. 1982.

Richard L. Dunn, et al., Monolithic Fibers for Controlled Delivery of Tetracycline, Southern Research Institute (pp. 157–159).

Thomas R. Tice, Controlled Release of Ampicillin and Gentamicin from Biodegradable Microcapsules, Southern Research Institute.

Roland Bodmeier, et al., Polylactic microspheres containing quinidine base and quinidine sulphate prepared by the solvent evaporation method. III. Morphology of the microspheres during dissolution studies, J. Microencapsulation, vol. 5, No. 4, pp. 323–330, 1988.

Marshall Devor, et al., Corticosteroids Suppress Ectopic Neural Discharge Originating in Experimental Neuromas, Pain, 22 pp. 127–137, (1985).

G. McCleane, M.D., et al., The addition of triarocinolone acetonide to bupivacaine has no effect on the quality of analgesia produced by ilioinguinal nerve block, Anaesthesia, vol. 49, pp. 819–820, 1994.

Naoki Wakiyama, et al., Influence of physiochemical properties of polylactic acid on the characteristics and in vitro release patterns of polylactic acid microspheres containing local anesthetics, Chem. Pharm. Bull, 30 (7), pp. 2621–2628, 1982.

Duncan H. Haynes, Ph.D., et al., Ultra–long–duration Local Anesthesia Produced by Injection Lecithin–coated Methoxyflurane Microdroplets, Anesthesiology, 63:490–499, 1985.

Costillo, et aL "Glucocorticosteroids Prolong Rat Sciatic Nerve Blockade in Vivo from Bupivacaine Microspheres", Anesthesiology, 85:1167–88 (1996).

Abstract: Nakano et al., "Biodegradable microspheres for Prolonged Anesthesia", HCAPLUS 102:209898 (1985).

Nakano et al., "Biodegradable microspheres for prolonged local anesthesia", Microspheres and Drug Therapy: Pharmaceutical, Immunological and Medical Aspects, pp 327–335 (1984).

Kajimaet al., "Preparation and Evaluation in Vitro of Polycarbonate Microspheres Containing Local Anesthetics", Chem. Pharm. Bull., 32(7) 2785–2802 (1984).

Physicians Desk Reference, "Marcaine", 51 Edition, pp. 2446–2448 (1997).

* cited by examiner

HIGH LOAD FORMULATIONS AND METHODS FOR PROVIDING PROLONGED LOCAL ANESTHESIA

This application is a continuation application of U.S. Ser. No. 08/714,782, filed Sep. 16, 1996, now U.S. Pat. No. 5,922,340, which is a continuation-in-part application of U.S. Ser. No. 08/432,402, filed May 1, 1995, now U.S. Pat. No. 5,700,485, which is a continuation-in-part of U.S. Ser. No. 08/119,958, filed Sep. 10, 1993, now U.S. Pat. No. 5,618,563, which is a continuation-in-part of Ser. No. 07/943,287, filed Sep. 10, 1992, now abandoned, the entire disclosures of which are hereby incorporated by reference.

The U.S. Government may have rights in this invention pursuant to National Institutes of Health Grant No. GM-1 5904 to Harvard Anesthesia Research and Teaching Center to C. Berde, and Grant No. CA 5257 to R. Langer.

FIELD OF THE INVENTION

The present invention is related to biocompatible controlled release formulations including formulations comprising surprisingly high loads of local anesthetic, for providing local anesthesia of sustained duration, as well as to methods for providing the same.

BACKGROUND OF THE INVENTION

While compounds utilized as general anesthetics reduce pain by producing a loss of consciousness, local anesthetics act via a loss of sensation in the localized area of administration in the body. The mechanism by which local anesthetics induce their effect, while not having been determined definitively, is generally thought to be based upon the ability to locally interfere with the initiation and transmission of a nerve impulse, e.g., interfering with the initiation and/or propagation of a depolarization wave in a localized area of nerve tissue. The actions of local anesthetics are general, and any tissue where nerve conduction, e.g., cell membrane depolarization occurs can be affected by these drugs. Thus, nervous tissue mediating both sensory and motor functions can be similarly affected by local anesthetics.

The duration of action of a local anesthetic is proportional to the time during which it is in actual contact with the nervous tissues. Consequently, previous attempts to prolong the duration of local anesthesia have focused on procedures or formulations that maintain localization of the drug at the nerve. For example, epinephrine is art known to briefly prolong the action of local anesthetics by inducing vasoconstriction adjacent to the site of injection. However, the duration of prolongation provided by epinephrine is on the order of about an hour, at best, in a highly vascularized tissue. This strategy is also severely limited by the risk of gangrene due to prolonged impairment of blood flow to local tissues.

The art has also attempted to prolong the duration of local anesthesia by providing more lipid-soluble compounds for use as long-acting anesthetics, i.e., local anesthetics that have a prolonged local anesthetic affect, but even these compounds provide a relatively limited duration of activity. For example, local anesthetics with a relatively short duration of action include, e.g., procaine with a duration of ranging from about 20–45 minutes, local anesthetics with an intermediate duration of action, e.g., lidocaine or mepivacaine, with a duration of action ranging from about 60–120 minutes and local anesthetics with a long duration of action, e.g., bupivacaine or etidocaine, with a duration ranging, under the most favorable circumstances, from about 400 to 450 minutes. However, this strategy for prolonging local anesthesia is limited by the possibility of local and systemic toxicity from excessive drug levels.

In fact, all local anesthetics are toxic, i.e., potentially toxic, and therefore it is of great importance that the choice of drug, concentration, rate and site of administration, as well as other factors, be considered in their use. On the other hand, as the preceding discussion makes clear, a local anesthetic must remain at the site long enough to allow sufficient time for the localized pain to subside.

Other pharmacological methods for prolonging local anesthesia have also been tried. European Patent Application No. 93922174.3 by Children's Medical, Center Corporation, discloses biodegradable synthetic polymers releasing local anesthetic over prolonged periods of time, as measured in vitro. Dexamethasone was included in the described formulation simply in order to avoid inflammation due to the polymer that was employed, however, the formulations described therein were of relatively low loading, e.g., microspheres with about 20% loading were exemplified, and it was taught by that publication that the duration of local anesthetic action was dependent upon the nature of the controlled release polymers described therein.

Other formulations directed to injectable microparticles and/or microcapsules, etc. are known. For example, U.S. Pat. No. 5,061,492 related to prolonged release microcapsules of a water-soluble drug in a biodegradable polymer matrix which is composed of a copolymer of glycolic acid and a lactic acid. The microcapsules are prepared as an injectable preparation in a pharmaceutically acceptable vehicle. The particles of water soluble drug are retained in a drug-retaining substance dispersed in a matrix of the lactic/glycolic acid copolymer in a ratio of 100/1 to 50/50 and an average molecular weight of 5,000–200,000. The injectable preparation is made by preparing a water-in-oil emulsion of aqueous layer of drug and drug retaining substance and an oil layer of the polymer, thickening and then water-drying. In addition, controlled release microparticles containing glucocorticoid agents are described, for example, by Tice et al. in U.S. Pat. No. 4,530,840.

In order to provide local anesthesia for extended periods, i.e., for more than about six hours, clinicians currently use local anesthetic agents administered through a catheter or syringe to a site where anesthesia is to be induced. Thus, prolonged local anesthesia, where the anesthesia is to be maintained over a period of greater than about 6 hours, has heretofore required that local anesthetic be administered either as a bolus or through an indwelling catheter connected to an infusion pump.

Thus, it has not heretofore been known to provide controlled release formulations with a relatively high loading of local anesthetic at a level that is substantially above 20% by weight, that is able to provide both a controlled release of local anesthetic and a substantially prolonged local anesthesia. It has also not heretofore been known to combine a formulation with a relatively high loading of a local anesthetic, e.g., substantially above 20% by weight, with a glucocorticosteroid agent in either immediate release or controlled release form, for providing prolonged local anesthesia that is achieved without a significant modification of the in vitro kinetics of local anesthetic release from the formulation.

OBJECTS OF THE INVENTION

It is therefore an object of the present invention to provide a controlled release dosage form for prolonged treatment of localized areas in humans and animals. More particularly, it is an object of the invention to provide formulations and methods for delivering a high load of local anesthetic in a biocompatible, controlled release form which provides a prolonged local anesthesia.

It is a further object of the present invention to provide a method for prolonging the effect of a local anesthetic agent at a desired site of treatment which is safe and effective, particularly for the control of post-operative pain.

It is a still further object to prolong the duration of the local anesthesia by administering a glucocorticosteroid agent (also referred to herein as glucocorticoid agents) in combination with a high loading of local anesthetic formulation or separately from the local anesthetic formulation, before, during or after the infiltration, injection or implantation of the compositions according to the invention.

SUMMARY OF THE INVENTION

In accordance with the above-mentioned objects and others, the invention is related to controlled release formulations for the prolonged administration of a high load, by weight percent, of a local anesthetic agent. In a preferred aspect, the high load controlled release local anesthetic is administered in combination with a glucocorticosteroid agent that is effective to prolong the duration of the local anesthetic effect, in vivo, for a time period greater than that possible by the use of the local anesthetic in controlled release form alone. Methods for the manufacture thereof are also disclosed. The controlled release formulation can be formed into slabs, pellets, microparticles, e.g., microspheres or microcapsules, spheroids and pastes suitable for insertion, implantation, injection, infiltration or topical application. Preferably, the formulation is in a form suitable for suspension in isotonic saline, physiological buffer and/or any other art-known vehicle acceptable for injection and/or infiltration into a patient.

The invention further provides methods for inducing localized anesthesia by implanting, inserting, infiltrating or injecting a controlled release formulation, e.g., in the form of injectable microspheres loaded with a relatively high loading of local anesthetic in sustained release form, into a site at or adjacent to a nerve or nerves innervating a body region to provide local anesthesia. Thus, the controlled release formulation according to the invention is injected, infiltrated, implanted or applied (e.g., topically) at a site in a patient where the local anesthetic agent is to be released.

Further aspects of the invention are directed to a method of treating a patient in need of a surgical procedure, comprising placing a local anesthetic in controlled release form adjacent to and/or in proximity to a nerve or nerves at the surgical site, and simultaneously and/or subsequently administering the aforementioned glucocorticosteroid agent to substantially the same site, to attain a prolongation of local anesthesia otherwise unattainable with the use of the local anesthetic alone.

The invention also provides for a unit dosage of the controlled release formulation comprising, in a container, a sufficient amount of the formulation to induce local anesthesia in at least one patient. In one embodiment, the unit dosages are sterile and lyophilized. Alternatively, the unit dosages are sterile and prepared as a suspension in a solution acceptable for injection into a patient.

The invention is further directed, in part, to novel formulations for providing local anesthesia, comprising a pharmaceutically-acceptable local anesthetic agent in controlled release form, said formulation being capable of being placed adjacent to and/or in proximity to a nerve which is to be anesthetized, and an effective amount of a glucocorticosteroid agent capable of prolonging the localized anesthetic effect provided by the local anesthetic in controlled release form. The glucocorticosteroid agent may be incorporated with the local anesthetic, or alternatively, at least part of the dose of the glucocorticosteroid agent may be administered separately but in proximity to the same location as the local anesthetic. At least a part of such a separate dose may be administered later in time than the local anesthetic, to provide additional prolongation of the extent and/or duration of the local anesthetic effect.

A portion of the local anesthetic can be administered to the desired site in immediate release form as long as a portion of the local anesthetic is also administered in controlled release form. In further embodiments, the invention is directed to a suspension comprising a plurality of controlled release, microparticles, e.g., microspheres and/or microcapsules comprising a local anesthetic agent, together with at least a portion of the glucocorticosteroid agent incorporated in the controlled release microparticles, or optionally, the glucocorticosteroid dissolved or suspended in a pharmacologically acceptable vehicle. The vehicle may be the same as that in which the microparticles are suspended, or may comprise a formulation for separate administration in controlled release and/or immediate release form in which the microparticles are suspended. The vehicle is, for example, suitable for administering the microparticles by injection. Optionally, at least a portion of the local anesthetic is incorporated into a controlled release formulation including a glucocorticosteroid agent coated on the surface thereof.

In yet additional embodiments of the invention, the formulation comprises a local anesthetic core and a glucocorticosteroid agent present in the core in an amount effective to prolong the effect of the local anesthetic in an environment of use, and a coating on the core that is effective to provide a slow release of the local anesthetic and glucocorticosteroid agent in an environment of use.

The glucocorticosteroid agent may also be systemically administered by injection, instillation, infiltration, oral dosing, topically or by any other art known method to obtain the desired prolongation of effect. Systemic administration (e.g., oral or intravenous) will require a higher total dose of a glucocorticosteroid agent than will local administration in proximity to the site of local anesthetic administration.

The controlled release local anesthetic dosage form may be injected, with or without a glucocorticosteroid agent, at the site where the anesthetic is to be released. This can be prior to surgery, at the time of surgery, or following removal (discontinuation) or reversal of a systemic anesthetic.

Examples demonstrate prolongation of the duration of local anesthesia with the greater prolongation being provided by the combination of a local anesthetic with a glucocorticosteroid agent.

Accordingly, the invention provides formulations with a high loading of local anesthetic by weight, relative to that heretofore available, to provide a prolonged localized local anesthesia. Surprisingly and unexpectedly, the formulations and methods according to the invention having relatively high drug loading, with relatively low proportions of controlled release carrier, allow for the sustained release of a local anesthetic agent and for a prolonged local anesthesia.

In addition, the administration of an effective amount -of at least one pharmaceutically acceptable glucocorticosteroid agent or agents, in conjunction with a local anesthetic agent in controlled release form, unexpectedly increases the duration of local anesthesia when both types of agent are administered at a site to be anesthetized, or to a site that has previously been anesthetized, in a patient.

DETAILED DESCRIPTION

Figure 1:
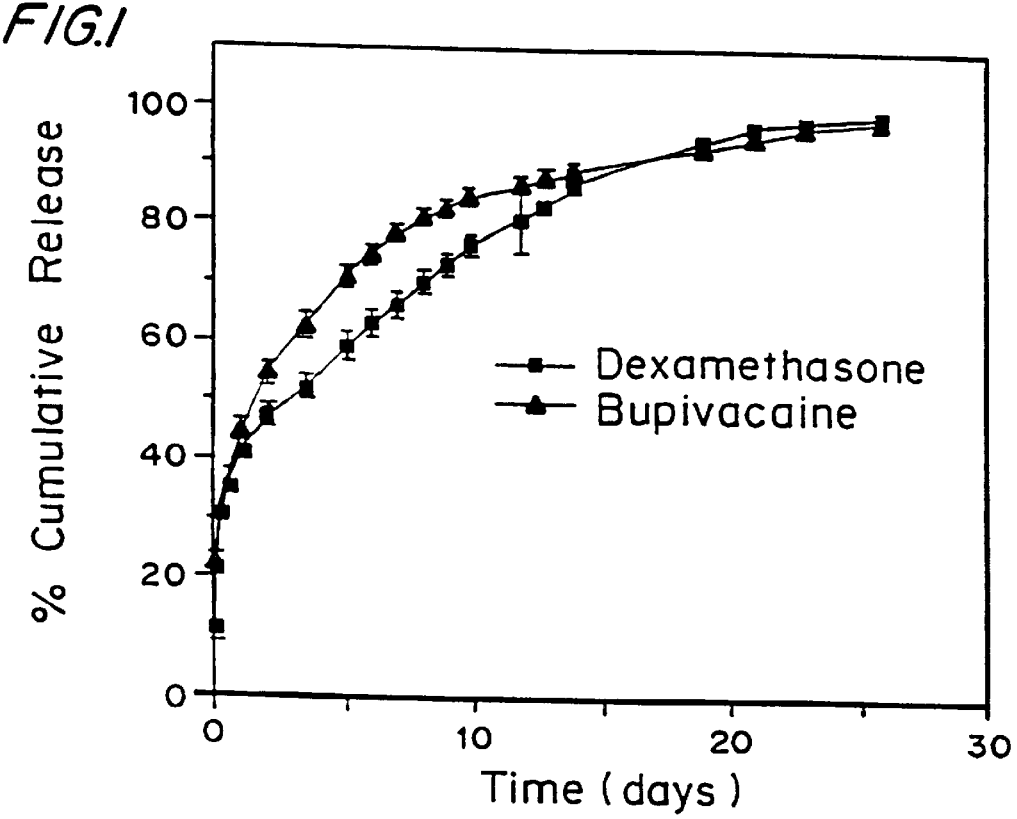
FIG. 1 is a graph of percent cumulative release of radio labeled bupivacaine versus time (days), in vitro, comparing microspheres containing either radiolabeled dexamethasone/unradiolabeled bupaivcaine containing microspheres and with radiolabeled bupivacaine/ unradiolabeled dexamethasone microspheres.

While the mechanism for glucocorticoid-induced prolongation of the duration of local anesthesia is not fully understood, it has been determined that the prolongation of local anesthesia provided by the formulations of the present invention cannot be predicted based entirely on the controlled release properties of the carrier used in the formulation, because of the relatively low proportions, e.g., about 25%, (w/w) of the carrier that is preferably employed, e.g., in microspheres comprising about 75% bupivacaine (w/w).

Further, it has been determined that the prolongation of the duration of local anesthesia by the use of a glucocorticosteroid agent cannot be predicted based on the in vitro release (dissolution) of the local anesthetic in controlled release form because the inclusion of the glucocorticosteroid agent within the controlled release formulations of the invention does not substantially alter or prolong the in vitro dissolution rate of the local anesthetic agent from the formulation. Instead, the same formulation when administered in vivo provides a significant increase in the time period of local anesthesia at the site of administration.

The glucocorticosteroid agents disclosed herein can be administered prior to, along with, or after injection of the local anesthetic agent in controlled release form, in each case with a substantial prolongation of local anesthesia, in vivo.

The glucocorticosteroid agent can be compounded in the same controlled release formulation as a local anesthetic agent, in a separate controlled release formulation, e.g., different injectable microspheres, or in a non-controlled release formulation.

In those embodiments of the invention directed to formulations where the glucocorticosteroid agent is included, the glucocorticosteroid agent may be included in controlled release form or in immediate release form. The glucocorticosteroid agent may be incorporated into the controlled release matrix along with the local anesthetic; incorporated into a controlled release coating on a sustained release device or formulation; or incorporated as an immediate release layer coating the local anesthetic formulation. On the other hand, the glucocorticosteroid agent may be incorporated into a pharmaceutically acceptable vehicle or medium suitable for topical administration, either in sustained release form or in immediate release form.

The controlled release formulations and methods of the invention may be used in conjunction with any implantable, insertable or injectable system known in the art, including but not limited to microspheres, microcapsules, gels, pastes, implantable rods, pellets, plates or fibers, and the like (generically referred to as "substrates").

As used herein, the term "local anesthetic agent" means any drug which provides local numbness and/or analgesia. Examples of local anesthetic agents which can be used include bupivacaine, ropivacaine, dibucaine, procaine, chloroprocaine, prilocaine, mepivacaine, etidocaine, tetracaine, lidocaine, and xylocaine, and mixtures thereof. The local anesthetic can be in the form of a salt, for example, the hydrochloride, bromide, acetate, citrate, carbonate or sulfate. More preferably, the local anesthetic agent is in the form of a free base. Preferred local anesthetic agents include, e.g., bupivacaine. For example, for bupivacaine, the free base provides a slower initial release and avoids an early "dumping" of the local anesthetic at the injection site. Other local anesthetics may act differently. Local anesthetic agents typically administered systematically may also be used in those cases where the means of administration results only in a local effect, rather than systemic. The term "local anesthesia" includes the conditions of, e.g., local numbness and/or analgesic and/or inhibitory. effects on motor function induced, simply by way of example, by a local anesthetic as defined above.

The term "local anesthetic" may also encompass, pursuant to the definitions provided herein, a drug of a different class than those traditionally associated with local anesthetic properties, including but not limited to morphine, fentanyl, and agents which, for example, can provide regional blockade of nociceptive pathways (afferent and/or efferent). The formulations according to the invention preferably provide high load formulations of controlled release local anesthetic agent.

The term, "local anesthesia" includes the condition of, e.g., a local numbness and/or analgesia, and/or inhibitory effects on sensory and motor function, induced, simply by way of example, by a local anesthetic as defined above.

The term, "controlled release" generally refers to compositions, e.g., pharmaceutically acceptable carriers, for controlling the release of an active agent or drug incorporated therein, typically by slowing the release of the active agent or drug in order to prevent immediate release. Such controlled release compositions and/or carriers are used herein to prolong or sustain the release of an active agent or drug incorporated, e.g., a local anesthetic and/or a glucocorticoid agent. Thus, the terms "controlled release" and "sustained release" are generally used interchangeably throughout this document unless otherwise indicated.

The phrase, "high load" or "high loading" as used herein indicates that the local anesthetic agent makes up substantially greater than 20% of the formulation, by weight. Thus, simply by way of example, a high load local anesthetic formulation comprises from about 30% loading to about 90% loading of local anesthetic relative to the total weight of the formulation, by weight. In a preferred aspect, a high load formulation comprises from about 60% to about 85% local anesthetic by weight, or even from about 70% to about 80% local anesthetic by weight. Most preferably, a high load formulation comprises about 75%, by weight, of local anesthetic agent, relative to the total weight of the formulation.

As used herein, the term "patient" broadly refers to any animal that is to be treated with the compositions and by the methods herein disclosed. The disclosed local anesthetic dosage form can provide localized anesthesia to any animal, e.g., any vertebrate, which it is desired to so anesthetize. In particular, the disclosed methods and compositions will find use in veterinary practice and animal husbandry for, e.g., birds and mammals, wherever prolonged local anesthesia is convenient or desirable. In a preferred embodiment, the term includes humans in need of or desiring prolonged local anesthesia.

The methods and formulations according to the invention may be applied, e.g., topically. Thus, any pharmaceutically acceptable formulation suitable for topical administration, e.g., to the skin or mucosal surfaces may be employed for administration of a local anesthetic and/or a glucocorticoid agent according to the invention, either as a single formulation or in separate formulations for inducing topical local anesthesia.

For internal administration, any formulation suitable for local implantation, infiltration or injection in proximity to a nerve that is able to provide a controlled release of a local anesthetic agent may be employed to provide for prolonged local anesthesia as needed. Slow release formulations or carriers known in the art include, e.g., emulsions, liposomes and liposome-like preparations, as well as specially coated pellets, polymer formulations or matrices for surgical insertion or as controlled release microparticles or microspheres for implantation, infiltration, insertion or injection, wherein the slow release of the active medicament is brought about through controlled diffusion out of the e.g., a carrier material and/or matrix and/or through selective breakdown of the coating of the preparation or selective breakdown of a polymer matrix.

The carrier material should be pharmaceutically acceptable, i.e., biocompatible and free from undesirable impurities. In the case of polymeric materials, biocompatability is enhanced using standard techniques designed to, remove undesirable impurities, e.g., by recrystallization of either the monomers forming the polymer and/or the polymer using standard techniques designed to remove undesirable impurities. Optionally, the biocompatible carrier may be biodegradable or non-biodegradable.

Simply by way of example, the controlled release carrier or material includes suitable biocompatible polymers. The polymeric material may comprise a polylactide, a polyglycolide, a poly(lactide-co-glycolide), a polyanhydride, a poblyorthoester, polycaprolactones, polyphosphazenes, polysaccharides, proteinaceous polymers, soluble derivatives of polysaccharides, soluble derivatives of proteinaceous polymers, polypeptides, polyesters, and polyorthoesters. The polysaccharides may be poly-1,4-glucans, e.g., starch glycogen, amylose, amylopectin, and mixtures thereof. The hydrophilic or hydrophobic polymer may be a water-soluble derivative of a poly-1,4-glucan, including hydrolyzed amylopectin, hydroxyalkyl derivatives of hydrolyzed amylopectin such as hydroxyethyl starch ES), hydroxyethyl amylose, dialdehyde starch, and the like. Preferred controlled release materials which are useful in the formulations of the invention include the polyanhydrides, co-polymers of lactic acid and glycolic acid wherein the weight ratio of lactic acid to glycolic acid is no more than 4:1 (i.e., 80% or less lactic acid to 20% or more glycolic acid by weight), and polyorthoesters containing a catalyst or degradation enhancing compound, for example, containing at least 1% by weight anhydride catalyst such as maleic anhydride. Other useful polymers include protein polymers such as gelatin and fibrin and polysaccharides such as hyaluronic acid. Since polylactic acid takes at least one year to degrade in vivo, this polymer should be utilized by itself only in circumstances where such a degradation rate is desirable or acceptable.

The polymeric material may be prepared by any method known to those skilled in the art. For example, where the polymeric material is comprised of a copolymer of lactic and glycolic acid, this copolymer may be prepared by the procedure set forth in U.S. Pat. No. 4,293,539 (Ludwig, et al.), hereby incorporated by reference. Basically, therein the copolymers are prepared by condensation of lactic acid and glycolic acid in the presence of a readily removable polymerization catalyst (e.g., a strong acid ion-exchange resin such as Dowex HCR-W2-H). The amount of catalyst is not critical to the polymerization, but typically is from about 0.01 to about 20 parts by weight relative to the total weight of combined lactic acid and glycolic acid. The polymerization reaction may be conducted without solvents at a temperature from about 100° C. to about 250° C. for about 48 to about 96 hours, preferably under a reduced pressure to facilitate removal of water and by-products. The copolymer is then recovered by filtering the molten reaction mixture to remove substantially all of the catalyst, or by cooling and then dissolving the reaction mixture in an organic solvent such as dichloromethane or acetone and then filtering to remove the catalyst.

Polyanhydrides may be prepared in accordance with the methods set forth in U.S. Pat. No. 4,757,128, hereby incorporated by reference. For example, polyanhydrides may be synthesized by melt polycondensation of highly pure dicarboxylic acid monomers converted to the mixed anhydride by reflux in acetic anhydride, isolation and purification of the isolated prepolymers by recrystallization, and melt polymerization under low pressure ($10^{-4}$ mm) with a dry ice/acetone trap at a temperature between 140°–250° C., for 10–300 minutes. High molecular weight polyanhydrides are obtained by inclusion of a catalyst which increases the rate of anhydride interchain exchange, for example, alkaline earth metal oxides such as CaO, BaO and $CaCo_3$. Polyorthoester polymers may be prepared, e.g., as set forth in U.S. Pat. No. 4,070,347, hereby incorporated by reference.

Various commercially available poly (lactide-co-glycolide) materials (PLGA) may be used in the preparation of the formulations, e.g., microspheres of the present invention. For example, poly(d,l-lactic-co-glycolic acid) are commercially available. A preferred commercially available product is a 50:50 poly (D,L) lactic co-glycolic acid. This product has a mole percent composition of 50% lactide and 50% glycolide. Other suitable commercially available products are (lactide: glycolide) 65:35 DL, 75:25 DL, 85:15 DL and poly(d,l-lactic acid) (d,l-PLA). For example, poly (lactide-co-glycolides) are commercially available from Boerhinger Ingelheim (Germany) under its ResomerC mark, e.g., PLGA 50:50 (Resomer RG 502), PLGA 75:25 (Resomer RG 752) and d,l-PLA (resomer RG 206), and from Birmingham Polymers (Birmingham, Alabama). These copolymers are available in a wide range of molecular weights and ratios of lactic to glycolic acid.

Pharmaceutically acceptable polyanhydrides which are useful in the present invention have a water-labile anhydride linkage. The rate of drug release can be controlled by the particular polyanhydride polymer utilized and its molecular weight. The polyanhydride polymer may be branched or linear. Examples of polyanhydrides which are useful in the present invention include homopolymers and copolymers of poly(lactic acid) and/or poly(glycolic acid), poly[bis(p-carboxyphenoxy)propane anhydride] (PCPP), poly[bis(p-carboxy)methane anhydride] (PCPM), polyanhydrides of oligomerized unsaturated aliphatic acids, polyanhydride polymers prepared from amino acids which are modified to include an additional carboxylic acid, aromatic polyanhydride compositions, and co-polymers of polyanhydrides with other substances, such as fatty acid terminated polyanhydrides, e.g., polyanhydrides polymerized from monomers of dimers and/or trimers of unsaturated fatty acids or unsaturated aliphatic acids. Polyanhydrides may be prepared in accordance with the methods set forth in U.S. Pat. No. 4,757,128, hereby incorporated by reference. For example, polyanhydrides may be synthesized by melt polycondensation of highly pure dicarboxylic acid monomers converted to the mixed anhydride by reflux in acetic anhydride, isolation and purification of the isolated prepolymers by recrystallization, and melt polymerization under low pressure ($10^{-4}$ mm) with a dry ice/acetone trap at a temperature between 140°–250° C. for 10–300 minutes. High molecular weight polyanhydrides are obtained by inclusion of a catalyst which increases the rate of anhydride interchain exchange, for example, alkaline earth metal oxides such as CaO, BaO and $CaCO_3$.

Polyorthoester polymers may be prepared, e.g., as set forth in U.S. Pat. No. 4,070,347, hereby incorporated by reference.

Proteinaceous polymers may also be used. Proteinaceous polymers and their soluble derivatives include gelation biodegradable synthetic polypeptides, elastin, alkylated collagen, alkylated elastin, and the like. Synthetic polypeptides include poly-(N-hydroxyalkyl)-L-asparagine, poly-(N-hydroxyalkyl)-L-glutamine, copolymers of N-hydroxyalkyl-L-asparagine and N-hydroxyalkyl-L-glutamine with other amino acids. Suggested amino acids include L-alamine, L-tysine, L-phenylalanine, L-valine, L-tyrosine, and the like.

In embodiments where the polymer comprises a gel, one such useful polymer is a thermally gelling polymer, e.g., polyethylene oxide, polypropylene oxide (PEO-PPO) block copolymer such as Pluronic® F 1 27 from BASF Wyandotte. In such cases, the local anesthetic formulation may be injected via syringe as a free-flowing liquid, which gels rapidly above 30° C. (e.g., when injected into a patient). The gel system then releases a steady dose of local anesthetic at the site of administration.

In additional embodiments, the controlled release material, which in effect acts as a carrier for the local anesthetic, can further include a bioadhesive polymer such as pectins (polygalacturonic acid), mucopolysaccharides (hyaluronic acid, mucin) or non-toxic lectins or the polymer itself may be bioadhesive, e.g., polyanhydride or polysaccharides such as chitosan. Definitions or further descriptions of any of the foregoing terminology are well known in the art and may be found by referring to any standard biochemistry reference text such as "Biochemistry" by Albert L. Lehninger, Worth Publishers, Inc. and "Biochemistry" by Lubert Stryer, W. H. Freeman and Company, both of which are hereby incorporated by reference.

The aforementioned biocompatible hydrophobic and hydrophilic polymers are particularly suited for the methods and compositions of the present invention by reason of their characteristically low human toxicity and virtually complete biodegradability.

In another embodiment, the carrier is a biocompatible, non-inflammatory and nonbiodegradable polymer such as, e.g., ethylene vinyl acetate ("EVA"). Such a nonbiodegradable polymer permits inserted or injected formulations to remain localized and able to be removed, intact, should that be required. Biodegradable carriers soften and lose their structural integrity over time, making the task of emergency removal difficult, if not impossible.

The substrates of the presently described formulations in certain preferred embodiments are manufactured using a method that evenly disperses the local anesthetic throughout the formulation, such as emulsion preparation, solvent casting, spray drying or hot melt, rather than a method such as compression molding. A desired release profile can be achieved by using a mixture of polymers having different release rates and/or different percent loading of local anesthetic and/or glucocorticosteroid agent, for example, polymers releasing in one day, three days, and one week. In addition, a mixture of microspheres having one or more different local anesthetic agents, having the same or different controlled release profile, can be utilized to provide the benefits of different potencies and spectrum of activity during the course of treatment.

In a preferred embodiment, a slow release formulation is prepared as microparticles, e.g., microcapsules and/or microspheres in a size distribution range suitable for local infusion, infiltration and/or injection. The diameter and shape of the microspheres or other particles can be manipulated to modify the release characteristics. For example, larger diameter microspheres will typically provide slower rates of release and reduced tissue penetration and smaller diameters of microspheres will produce the opposite effects, relative to microspheres of different mean diameter but of the same composition. Optionally, other particle shapes, such as, for example, cylindrical shapes, can also modify release rates by virtue of the increased ratio of surface area to mass inherent to such alternative geometrical shapes, relative to a spherical shape. The diameter of injectable -microspheres are in a size range from, for example, from about 5 microns to about 200 microns in diameter. In a more preferred embodiment, the microspheres range in diameter from about 20 to about 120 microns.

Methods for manufacture of microspheres are well known and are typified in the following examples. Examples of suitable methods of making microspheres include solvent evaporation, phase separation and fluidized bed coating.

In solvent evaporation procedures, the local anesthetic agent, if soluble in organic solvents, may be entrapped in the polymer by dissolving the polymer in a or volatile organic solvent, adding the drug to the organic phase, emulsifying the organic phase in water which contains less than 5% polyvinyl alcohol, and finally removing the solvent under vacuum to form discrete, hardened monolithic microspheres.

Phase separation microencapsulation procedures are suitable for entrapping water soluble agents in the polymer to prepare microcapsules and microspheres.

Phase separation involves coacervation of the polymer from an organic solvent by addition of a nonsolvent such as silicone oil.

In fluidized bed coating, the drug is dissolved in an organic solvent along with the polymer. The solution is then processed, e.g., through a Wurster air suspension coater apparatus to form the final microcapsule product. Other methods of microsphere preparation are described in co-owned U.S. Ser. No. 08/714,783, filed on even date herewith, the disclosure which is incorporated by reference herein in its entirety.

For example, the microspheres may be obtained by utilizing a solvent extraction technique (reactor process) which involves dissolving the drug and the polymer in an organic solvent such as ethyl acetate. This solution thereby obtained (the dispersed phase) is added to a solution of, e.g., polyvinyl alcohol (PVA) in water (the continuous phase) with stirring. The emulsion thereby formed is then added to water in order to extract the solvent and to harden the microspheres. The mixture is then filtered and the microspheres are dried. One appropriate method of drying is, e.g., under vacuum at room temperature. Optionally, the microsphere may be dried by a freeze drying process. The desired particle size fraction is then collected by sieving. The organic solvent utilized is preferably ethyl acetate; however, any pharmaceutically acceptable organic solvent may be utilized, such as acetone, ethanol, diethyl ether, methanol, benzyl alcohol, methylene chloride, petroleum ether or others. This procedure is particularly useful for preparing microspheres of e.g., bupivacaine base or free-base forms of glucocorticoids.

Alternatively, the microspheres of bupivacaine base and/or glucocorticoid may be prepared by dissolving the drug and polymer in ethyl acetate and thereafter spray drying the solution.

In instances where the microspheres are to incorporate drugs which are very water soluble and insoluble in ethyl acetate, such as bupivacaine HCl and/or water soluble glucocorticoids, the microspheres may be prepared using a coacervation/phase separation rather than the solvent extraction technique described above. However, the solvent extraction technique can be used with e.g., bupivacaine HCl and/or water soluble glucocorticoids due to its low water solubility at pH 7.4 and above. The coacervation/phase separation technique utilized involves dissolving the polymer in ethyl acetate and suspending micronized bupivacaine HCl in the solution. Silicone oil is then added to-form the microspheres. This mixture is then added to heptane to harden the microspheres, which are then separated by filtration. The microspheres are dried under a vacuum at room temperature. The desired particle size fraction is then collected by sieving.

Alternatively, micropheres prepared using bupivacaine HCl and/or glucocorticoids may be accomplished by suspending the drug in a solution of polymer in ethyl acetate or in methylene chloride and methanol and spray drying.

Alternatively, the drug or drugs may be dissolved in water, and the polymer may be dissolved in ethyl acetate. The water phase then can be added to the organic phase and either homogenized or sonicated to yield a W/O emulsion. The drug being in the water phase would then be surrounded by polymer (oil phase). This is then added, e.g., paired into, PVA solution in water with homogenization to form a W/O/W emulsion. The solvent diffuses out, leaving microspheres. Additional cold water can be added to harden the microspheres. This process may yield more uniform microspheres without requiring micronization of the drug. Also, as the drug will be surrounded by polymer, the release of the drug may be more uniform and be diffusion-controlled.

The biocompatible controlled release materials may optionally be used in order to prepare controlled release local anesthetic implants. The implants may be manufactured, e.g., by compression molding, injection molding, and screw extrusion, whereby the local anesthetic agent is loaded into the polymer. Implantable fibers can be manufactured, e.g., by blending the local anesthetic agent with the controlled release material and then extruding the mixture, e.g., under pressure, to thereby obtain biocompatible fibers. In certain preferred embodiments, the glucocorticosteroid agent may be incorporated into the implant, or may be coated onto a surface of the implant.

In other embodiments of the invention, the controlled release material and/or carrier comprises, pharmaceutically acceptable emulsions, including oil in water and water in oil emulsions, gels, gums and matrices suitable for controlled release of local anesthetics and/or glucocorticoids an artificial lipid vesicle, or liposome. Simply by way of example, liposomes are well known in the art as carriers of bioactive or pharmacologically active substances such as drugs. Liposomes as described herein will vary in size. Preferably, the liposomes have a diameter between 100 nm and 10 microns or greater. A wide variety of lipid materials may be used to form the liposomes including natural lecithins, e.g., those derived from egg and soya bean, and synthetic lecithins, the proviso being that it is preferred that the lipids are non-immunogenic and biodegradable. Also, lipid-based materials formed in combination with polymers may be used, such as those described in U.S. Pat. No. 5,188,837 to Domb, (incorporated by reference herein in its entirety).

Examples of synthetic lecithins which may be used together with their respective phase transition temperatures, are di-(tetradecanoy)phosphatidylcholine (DTPC) (23° C.), di-(hexadecanoyl)phosphatidylcholine ODBPC) (41° C.) and di-(octandecanoyl) phosphatidylcholine (DOPC) (55° C.). Di-(hexadecanoyl) phosphatidycholine is preferred as the sole or major lecithin, optionally together with a minor proportion of the di-(octadecanoyl) or the di-(tetradecanoyl) compound. Other synthetic lecithins which may be used are unsaturated synthetic lecithins, for example, di-(oleyl) phosphatidyl-choline and di-linoleyl)phosphatidylcholine. In addition to the main liposome-forming lipid or lipids, which are usually phospholipids, other lipids (e.g. in a proportion of 5–40% w/w of the total lipids) may be included, for example, cholesterol or cholesterol stearate, to modify the structure of the liposome membrane, rendering it more fluid or more rigid depending on the nature of the main liposome-forming lipid or lipids.

In certain embodiments, the glucocorticosteroid agent is incorporated along with the local anesthetic agent into the lipid. In other preferred formulations, the lipids containing the local anesthetic agent are dispersed in a pharmaceutically acceptable aqueous medium. The glucocorticosteroid agent may be incorporated into this aqueous medium. In a further embodiment, a portion of the dose of the local anesthetic is incorporated into the aqueous medium in immediate release form. The resultant formulation is an aqueous suspension which may comprise the local anesthetic and/or glucocorticosteroid agent partitioned between a free aqueous phase and a liposome phase.

As an even further alternate embodiment, liposomes containing local anesthetic may be combined in an aqueous phase where liposomes containing the glucocorticosteroid agent to form an aqueous pharmaceutical suspension useful for administration at the desired site in the patient to be anesthetized. This may be accomplished via injection or implantation. Liposomes may be prepared by dissolving an appropriate amount of a phospholipid or mixture or phospholipids together with any other desired lipid soluble components (e.g., cholesterol, cholesterol stearate) flowing in a suitable solvent (e.g., ethanol) and evaporating to dryness. An aqueous solution of the local anesthetic, optionally with glucocorticosteroid agent, may then be added and mixed until a lipid film is dispersed. The resulting suspension will contain liposomes ranging in size, which may then fractionated to remove undesirable sizes, if necessary. This fractionation may be effected by column gel chromatography, centrifugation, ultracentrifugation or by dialysis, as well known in the art.

The above method of preparation of liposomes is representative of a possible procedure only. Those skilled in the art will appreciate that there are many different methods of preparing liposomes, all of which are deemed to be encompassed by the present disclosure.

In additional embodiments of the invention, the substrate comprises a plurality of microcapsules laden with the local anesthetic agent with or without the glucocorticosteroid agent. Microcapsules may be prepared, for example, by dissolving or dispersing the local anesthetic agent in an organic solvent and dissolving a wall forming material (polystyrene, alkylcelluloses, polyesters, polysaccharides, polycarbonates, poly(meth)acrylic acid ester, cellulose acetate, hydroxypropylmethylcellulose phthalate, dibutylaminohydroxypropyl ether, polyvinyl butyral, polyvinyl formal, polyvinylacetal-diethylamino acetate, 2-methyl-5-vinyl pyridine methacrylate-methacrylic acid copolymer, polypropylene, vinylchloride-vinylacetate copolymer, glycerol distearate, etc.) in the solvent; then dispersing the solvent containing the local anesthetic agent and wall forming material in a continuous-phase processing medium, and then evaporating a portion of the solvent to obtain microcapsules containing the local anesthetic agent in suspension, and finally, extracting the remainder of the solvent from the microcapsules. This procedure is described in more detail in U.S. Pat. Nos. 4,389,330 and 4,530,840, hereby incorporated by reference.

The controlled release dosage forms of the present invention preferably provide a sustained action in the localized area to be treated. For example, it would be desirable that such a formulation provides localized anesthesia to the site for a period of one day, two days, three days, or longer. The formulations can therefore, of course, be modified in order to obtain such a desired result.

Microspheres and other injectable substrates described herein may be prepared incorporated with a pharmaceutically acceptable solution vehicle, such as a isotonic saline and/or other buffer aqueous solution or suspension for injection. The viscosity of the final reconstituted product is preferably in a range suitable for the route of administration. In certain instances, the final reconstituted product viscosity may be, e.g., about 35 cps. Administration may be via the subcutaneous or intramuscular route. However, alternative routes are also contemplated, and the formulations may be applied to the localized site in any manner known to those skilled in the art including topical application, localized injection or infiltration, localized intra arterial nerve block, and the like, such that a localized effect is obtained. The substrate formulations of the invention can also optionally be implanted, e.g., surgically or by means of a probe, at the site to be treated. Thus, the formulations of the present invention, when including a local anesthetic, may be used in the control of post-operative pain.

Depending on the potency of the desired local anesthetic and upon the desired weight of the resulting formulation, the anesthetic is incorporated into the polymer or other controlled-release formulation in a percent loading between 0.1% and 90% by weight. Preferably the anesthetic is incorporated as a high load formulation comprising from about between about 30% loading to about 90% loading by weight. Preferably, a high load comprises from about 60% to about 85% by weight, loading or even from about 70% to about 80% loading by weight. Most preferably, a high load comprises about 75% loading, by weight, of local anesthetic agent.

It is also possible to tailor a system to deliver a specified loading and subsequent maintenance dose by manipulating the percent drug incorporated in the polymer and the shape of the matrix or formulation, in addition to the form of local anesthetic (e.g., free base versus salt) and the method of production. Heretofore it has been believed that the amount of drug released per day increases proportionately with the percentage of drug incorporated into the formulation, e.g., matrix (for example, from 5 to 10 to 20%). Based on this previously observed proportional relationship the ordinary artisan would have previously believed that high loadings of drug would result in rapid release or dumping of the local anesthetic at the injection or implantation site, resulting a shortened of action and unacceptable levels of local tissue irritation or even local tissue toxicity.

However, in a surprising discovery, it has been found that at high drug loadings according to the present invention, the proportional relationship between drug loading and release rates does not apply. For example, according to the preferred embodiment, polymer matrices or other formulations with about 75% drug incorporated are utilized to provide both a rapid onset of local anesthesia and a prolonged release of local anesthesia. It is also possible to incorporate substantially more drug, depending on the drug, the method used for making and loading the carrier, e.g., a controlled release polymer so that an acceptable release rate is obtained. The use of glucocorticosteroid to prolong the local anesthesia further enhances the unexpectedly beneficial result of using high drug loadings.

When a glucocorticosteroid agent is included in the controlled release substrates comprising local anesthetic, it has been found that useful loadings of glucocorticosteroid agent are, e.g., from 0.005% to 30% by weight of the substrate.

When the glucocorticosteroid agent is included with a suitable vehicle in which microparticles comprising local anesthetic are suspended, the glucocorticosteroid agent is present, for example, in a weight percent relative to the local anesthetic varying from about 0.005% to about 15%.

The artisan will appreciate that the dosage of the controlled release formulations is dependent upon the kind and amount of the drug to be administered, the recipient animal, and the objectives of the treatment. For example, when the drug included in the microspheres of the present invention is bupivacaine, the bupivacaine content of the formulation ranges from, e.g., about 0.5 to about 450 mg/kg body weight. The effective dose of bupivacaine, or an amount of another local anesthetic sufficient to provide proportional potency, can range from about 1 to about 600 mg, or more, of bupivacaine injected or inserted at each site where the release of a local anesthetic agent is desired. In certain preferred embodiments, the dose of bupivacaine in the controlled release dosage form of the invention is sufficient to provide a controlled release of about 8 to about 30 mg per hour at the release site for at least 1 to 4 days. Since the formulations of the present invention are controlled release, it is contemplated that formulations may include much more than usual immediate release doses, e.g., as much as 120 mg of drug per kg of body weight, or more.

In certain preferred embodiments, the controlled release substrate comprising local anesthetic is characterized by in vitro release rates of about 10 to about 60 percent release of local anesthetic after 24 hours, from about 20 to about 80 percent release after 48 hours and from about 40 to about 100 percent release, after 72 hours. More preferably, the controlled release substrate comprising local anesthetics characterized by in vitro release rates of about 25 to about 40 percent release of local anesthetic after 24 hours, from about 40 to about 50 percent release after 24 hours and from about 45 to about 55 percent release after 72 hours and 80 to 100 percent cumulative release is provided after about 280 hours.

In order to obtain a prolonged local anesthetic effect in vivo when combined with the glucocorticosteroid agent as described herein, the glucocorticosteroid agent is placed into approximately the same site in a patient (e.g., human or veterinary) before, simultaneously with, or after the placement of a local anesthetic at that site. The presence of glucocorticosteroid agent in the controlled release formulation does not significantly affect the in vitro or in vivo release rates of local anesthetic.

In a preferred embodiment the local anesthetic effect is prolonged by the use of an glucocorticosteroid agent from about 1.1 to about 14 fold or more of the duration local anesthetic effect that is obtained from the same formulation without benefit of an glucocorticosteroid agent. In a further preferred embodiment, the prolongation ranges from about 1 to about 13 fold, or even from about 6 to about 13 fold of the duration of local anesthesia induced by controlled release local anesthetic without glucocorticosteroid enhancement.

The duration of the local anesthetic effect prolonged by an glucocorticosteroid agent ranges, e.g., from about 0.1 to about 200 hours or more, from about 1 to about 150 hours, from about 24 to about 150 hours and from about. 24 to about 100 hours, of local anesthesia from the time of administration of the local anesthetic.

The rate of release of local anesthetic agent or other drugs incorporated into the formulation will also depend on the solubility properties of the local anesthetic or drug. The greater the solubility in water, the more rapid the rate of release in tissue, all other parameters being unchanged. For example, those local anesthetic agents having pH dependent solubility will be released more rapidly at the optimum pH for those compounds. The greater the solubility in water, the more rapid the rate of release in tissue, all other parameters being unchanged. For example, those local anesthetic agents having pH dependent solubility will be released more rapidly at a pH lower than the pKa value for each such compound. For example, in one embodiment, the formulation will have released, in vitro, at least 70 percent of a local anesthetic at 48 hours at about pH 6 and will have released at least 40 percent of a local anesthetic at a pH ranging from about 7.4 to about 8, at 48 hours. Other combinations are pH independent in their release.

The examples demonstrate that the above-described glucocorticosteroid agents prolong the duration of local anesthesia in vivo and do not significantly alter the time course of release of bupivacaine in vitro.

Potential applications include any condition for which localized anesthesia is desirable. This includes both the relief of pain and motor symptoms as well as local anesthesia, e.g., localizes inhibition of nerve transmission, for other medical purposes. The formulations and methods according to the invention can be used to provide two to five day intercostal anesthesia for thoracotomy, or longer term intercostal anesthesia for thoracic post-therapeutic neuralgia, lumbar sympathetic anesthesia for reflex sympathetic dystrophy, or three-day ilioinguinal/iliohypogastric blockade for hernia repair.

Other potential applications include obstetrical or gynecological procedures. Yet further potential applications include providing localized temporary sympathectomy, e.g., blockade of sympathetic or parasympathetic ganglia to treat a variety of autonomic diseases, including circulatory dysfunction or cardiac dysrhythmias. The formulations may also be used to treat trigeminal neuralgia and other diseases of the cranial nerves as well as to provide temporary nerve blockade to treat localized muscle spasm and treatment of retrobulbar conditions, e.g., eye pain. Other uses include intra-operative administration in order to reduce pain during and after the operative procedure, especially for plastic surgery procedures where prolonged anesthesia will enhance the outcome.

These systems can also be used for the management of various forms of persistent pain, such as postoperative pain, sympathetically maintained pain, or certain forms of chronic pain such as the pain associated with many types of cancer.

These systems may also be used for anesthetizing nociceptive pathways (afferent and efferent) in patients with acute pancreatitis, ileus, or other visceral disorders. These are merely examples, and additional uses for both human and veterinary practice are immediately apparent to the artisan.

Methods of Administration

Further to the above discussion, it will be appreciated that, in a preferred method of administration a dosage form, e.g., microspheres, are administered topically e.g., by application and/or by infusion, infiltration and/or injection into a site where local anesthetic agent is to be released. Microspheres may be injected through a syringe or a trochar. Dosage forms such as pellets, slabs, spheroids and the like may also be optionally surgically placed into a site where release of oral anesthetic agent is desired.

As described below, microspheres according to the invention can be administered alone or in combination with a carrier including a glucocorticosteroid agent, e.g., dissolved and/or suspended in a carrier, e.g., as a solution or suspension in an amount effective to prolong the duration of local nerve blockade. Alternatively, the microspheres include an amount of glucocorticosteroid agent effective to prolong the duration of local nerve blockade.

In another alternative, one or more glucocorticosteroid agents can be administered before, simultaneously with or after administration of the controlled release local anesthetic, wherein the glucocorticosteroid is formulated into a separate microsphere formulation for controlled release. The controlled release rate for the glucocorticosteroid agents may be the same as or different than the controlled release rate for the local anesthetic. In a further embodiment, it has been found that additional dose of glucocorticosteroid agent may also be administered as an injectable solution or suspension, in an injectable carrier or in a controlled release carrier to the nerve to be blockaded after the controlled release local nerve blockade has worn off, in order to reactivate the initial nerve blockade without the co-administration of additional local anesthetic.

The microspheres may be prepared from PLGA polymers ranging from, for example, PLGA in a ratio of 50:50, 65:35 or 75:25. An optimum composition has been determined to be PLGA 65:35.

The artisan will appreciate that, as with all local anesthetics, the dosage of local anesthetic containing microspheres will vary and will depend, simply by way of example, upon the area to be anesthetized, the vascularity of the tissues, the number of neuronal .segments to be treated, the size and weight of the patient (e.g., veterinary practice, human child, human adult) individual tolerance and the technique of anesthesia. Of course, under normal circumstances, the lowest dosage need to provide effective anesthesia should be administered.

The microspheres, formulated with, e.g., PLGA 65:35 microspheres are administered in a dose ranging from, for example, 1 through 450 mg per kg of body weight, of microspheres 75% (w/w) loaded with a local anesthetic such as bupivacaine, per kg of body weight. In a preferred embodiment the dose ranges from 5 through 250 mg of microspheres/kg of body weight. In a more preferred embodiment the dose ranges from about 10 to about 150 mg of microspheres/kg of body weight, with PLGA 65:35.

An effective dose of a local anesthetic, such as bupivacaine, is typically administered in microspheres comprising, e.g., 75% by weight bupivacaine, and can range from about 0.5 to about 1000 mg, or more, of bupivacaine, depending on the site to be anesthetized, the number of segments to be anesthetized and the patient, as discussed above. Preferably, a dose ranging from about 1 mg to about 500 mg of bupivacaine is administered, or even a dose ranging from about 5 mg to about 100 mg of bupivacaine is administered at the site and/or sites to be anesthetized.

Certainly, the artisan will appreciate the fact that the dose ranges mentioned above are based on the potency of bupivacaine, and that exact effective dosages will vary will the particular relative potency and pharmacokinetics of each local anesthetic and will be able to readily adjust the dose according to the degree of anesthesia experienced by the patient.

The formulation described herein can also be used to administer local anesthetic agents that produce modality-specific anesthesia, as reported by Schneider, et al., *Anesthesiology*, 74:270–281 (1991), or that posses physical chemical attributes that make them more useful for sustained-release then for single injection anesthesia, as reported by Masters, et al., *Soc. Neurosci. Abstr.* 18:200 (1992), the teachings of which are incorporated herein.

Administration of formulations according to the invention may require the use of a vehicle, e.g., any vehicle that is pharmaceutically acceptable for desired route of administration. Thus, for topical administration or application, the formulations prepared according to the invention comprising local anesthetic and/or glucocorticoid may be dissolved e.g., for immediate release forms) or suspended (e.g., for microparticles) in vehicles including buffered solutions, e.g., saline solution, including, e.g, hypotonic and/or buffered saline, as well as in creams, ointments, oils, emulsions, liposomes and the like and/or any other art-known pharmaceutically acceptable topical vehicle. For administration by injection and/or infiltration, the formulations according to the invention may be suspended (e.g., for microparticles), or dissolved (e.g., for immediate release forms), in any art-known vehicle suitable for injection and/or infiltration. Such vehicles include, simply by way of example, isotonic saline, buffered or unbuffered and the like and may optionally include any other art known ingredients or agents, e.g., colorants, preservatives, antibiotics, epinephrine and the like. A more complete listing of art-known vehicles for administration of formulations topically, by systemic administration and/or local injection and/or-infiltration is provided by reference texts that are standard in the art, for example, *REMNGTON's PHARMACEUTICAL SCIENCES*, 16th Edition, 1980 and 17th Edition, 1985, both published by Mack Publishing Company, Easton, Pa., the disclosures of which are incorporated by reference herein in their entireties.

The use of the above-described glucocorticosteroid agents before, simultaneously with or after administration of a high load formulation of a controlled release local anesthetic, results in prolonged anesthesia relative to the derivation of anesthesia induced by an equivalent formulation without co-administration of glucocorticoid.

Clinical Utility

It will also be appreciated that the high load local anesthetic formulations and methods according to the invention can generally employed in any art known localized anesthesiological procedures. For example, for surface anesthesia, microparticle suspensions or other forms of controlled release carrier, e.g., microsphere, cellulose based polymers and/or gum matrices in paste form, suitable for topical application, are used to anesthetize mucous membranes, skin and for ophthalmological use. Effective amounts of glucocorticoid agents can be included with the topical controlled release formulation or, optionally, at least a portion of the glucocorticoid agent can be separately administered in controlled release form, immediate release form and/or a combination thereof.

In addition, the high load local anesthetic formulations and methods according to the invention can be used for infiltration anesthesia, wherein a formulation suitable for injection is injected directly into the tissue requiring anesthesia. For example, an effective amount of the formulation in injectable form is infiltrated into a tissue area that is to be incised or otherwise requires local anesthesia. In addition, the local anesthetic formulations and methods according to the invention can be used for field block anesthesia, by injecting an effective amount of the formulation in injectable form in such a manner as to interrupt nerve transmission proximal to the site to be anesthetized. For instance, subcutaneous infiltration of the proximal portion of the volar surface of the forearm results in an extensive area of cutaneous anesthesia that starts 2 to 3 cm distal to the site of injection. Simply by way of example, the same effect can be achieved for the scalp, anterior abdominal wall and in the lower extremities. Effective amounts of glucocorticoid agents can be included with injectable controlled release formulation or, optionally, at least a portion of the glucocorticoid agent can be separately administered in controlled release form, immediate release form and/or a combination thereof.

Further, for even more efficient results, the high load local anesthetic formulations and methods according to the invention can be used for nerve block anesthesia. For example, an effective amount of the formulation in injectable form is injected into or adjacent to individual peripheral nerves or nerve plexuses. Injection of an effective amount of a high load local anesthetic formulation according to the invention into mixed peripheral nerves and nerve plexuses can also desirably anesthetize somatic motor nerves, when required. The high load formulations and methods according to the invention can also be used for intravenous regional anesthesia by injecting a pharmacologically effective amount of microspheres in injectable form into a vein of an extremity that is subjected to a tourniquet to occlude arterial flow.

Further still, spinal and epidural anesthesia using high load formulations, e.g., injectable microspheres and methods according to the invention will be appreciated by the artisan to be within the scope contemplated by the present invention.

The formulation described herein can also be used to administer local anesthetic agents that produce modality-specific blockade or anesthesia effect, as reported by Schneider, et al., *Anesthesiology*, 74:270–281 (1991).

DETAILED DESCRIPTION OF THE PREFERRED EMBODIMENTS

The following non-limiting examples illustrate the preparation of the formulations according to the invention and the effects of local anesthetic and glucocorticosteroid agents alone and in combination.

Example 1

Prolonged nerve blockade with steroidal anti-inflammatories
As demonstrated by the following study:
(1) Bupivacaine-polyester microspheres can be formulated with mechanical stability at very high percent drug loading, for example, up to 75% by weight.
(2) Bupivacaine-polyester microspheres with high percent loading have controlled release of drug, and do not produce rapid initial burst release of drug in vitro or in vivo.

Methods and Material

Abbreviations include PLGA, poly-lactic-glycolic acid; $CH_2Cl_2$, methylene chloride; dpm, disintegrations per minute; cpm, counts per minute; rpm, revolutions per minute.

The non-radioactive polymer microspheres used in this study were obtained from a commercial source. Tritium labeled dexamethasone was obtained from Amersham (specific activity $9.24 \times 10^{10}$ dpm/$\mu$mole). Bupivacaine free base was supplied by Purdue Frederick and dexamethasone was supplied by Sigma. Trisma base was supplied by Sigma. Dulbecco's phosphate-buffered saline was supplied by Gibco, Md. (KCL 2.68 mM/L, $KH_2PO_4$ 1.47 mM/L, NaCl 547.5mM/L, $NaBPO_4$ 9.50 mM/L). The suspension media used in the in vivo experiments was consisted of 0.5% w/v sodium carboxymethylcellulose (medium viscosity) and 0.1% w/v Tween 80. A Coulter® Multisizer II, Coulter Electronics Ltd., Luton, England was used to determine the mass median diameter of the microspheres.

Polymer synthesis and Local Anesthetic Incorporation

The radiolabeled microspheres were formulated by a single emulsion technique, using an evaporation process. Two types of radiolabeled microspheres were formulated, one which contained 75% w/w unlabeled bupivacaine and 0.05% w/w tritium labeled dexamethasone and the other contained 0.05% w/w unlabeled dexamethasone and 75% w/w tritium labeled bupivacaine. The micro spheres which contained tritium labeled dexamethasone were prepared as follows: an aliquot of dexamethasone containing $8 \times 10^6$ disintegrations per minute (dpm) was added to 100 $\mu$ls of a solution of 5 mg of unlabeled dexamethasone in 5 mls of ethanol. The sample was dried under a stream of nitrogen for one hour and 50 mg of PLGA 65:35 and 150 mg of bupivacaine free base in 1 ml of $CH_2CL_2$ were added. The tube was vortexed for 1 minute at 2000 rpm on a Fisher Scientific Touch Mixer, Model 232. Then 1 ml of 0.3% polyvinylalcohol in 100 mM Trisma®D (tris (hydroxymethyl)amino methane) base (pH adjusted to 8.4) was added, and an emulsion formed by vortexing for 45 seconds. The emulsion was then poured into 100 mls of 0.1% polyvinylalcohol in 100 mM Trisma® base. The $CH_2CL_2$ was removed from the microspheres using a rotary evaporator under vacuum at 31° C. for 20 minutes. After 2–3 minutes bubbles formed indicated that the organic solvent was being removed. The microspheres were sieved through a series of stainless steel sieves of pore sizes 140$\mu$, 60$\mu$ and 20$\mu$ (Neward Wire Co.). Those microspheres which were less than 20 and greater than 140 microns in diameter were discarded. The microspheres which fell in the size range 20$\mu$ to 140$\mu$ were centrifuged at 4000 rpm for 5 minutes, rinsed with buffer and centrifuged again. The microspheres were then frozen in liquid nitrogen and lyophilized overnight. The microspheres were examined before and after solvent removal using an American Optical One—Ten light microscope to ensure that no leaching of the drug took place. If leaching did occur, the bupivacaine crystallized and could be seen even at 10× using a light microscope.

The microspheres which contained tritium labeled bupivacaine were formulated as described above with the following exceptions: An aliquot of radiolabeled bupivacaine consisting of $9 \times 10^6$ dpm was added to 150 mg of unlabeled bupivacaine free base. The solution was then vortexed to ensure homogeneous mixing of labeled and unlabeled bupivacaine. The ethanol was then removed under a stream of nitrogen for 1 hour. Upon removal of the ethanol, 50 mg of PLGA 65:35 and 100 $\mu$l from a solution dexamethasone 1 mg/ml in ethanol were added. Thereafter, the protocol was the same as that used to formulate microspheres which contained radiolabeled dexamethasone.

In order to determine the drug content, 5 mg of microspheres were dissolved in 2 mls of $CH_2Cl_2$ and the local anesthetic concentration determined by U.V. spectroscopy. The absorbance at 272 nm was read and compared to a. calibration curve of known amounts (0 to 2.5 mg/ml) of bupivacaine free base dissolved in $CH_2Cl_2$.

In Vitro Release studies

Unlabeled Microspheres 5 mg of microspheres were weighed out and 2 mls of Dulbecco's phosphate-buffered saline was added. The pH of the buffer was adjusted to 7.4 and 0.1% sodium azide was added as an antimicrobial agent. The buffer was changed at 0.5, 2, 6, 12, and 24 hours and once daily thereafter. The amount of bupivacaine free base in the buffer was determined using a Hewlett Packard 8452 Diode Array Spectrophotometer at 272 nm. Duplicates from each batch of microspheres were assayed. Release media incubated with control microspheres which did not contain bupivacaine showed insignificant absorbance at 272 nm.

Labeled Microspheres

The procedure used to determine the in vitro release of both bupivacaine and dexamethasone is the same as that used for non-radiolabeled microspheres, except that the amount of radiolabeled compound released into the buffer was determined by adding 17 mls of Ecolume® scintillation fluid to 2 mls of buffer. The total number of counts was determined using a LKB Wallac 1214 Rackbeta Liquid Scintillation Counter. The efficiency, (the counts per minute/disintegration per minute), of the counter was determined to be 51%. Five replications of each set of radiolabeled microspheres were used.

Preparation of Microsphere Suspensions for In Vivo Testing

The dose used varied between 50 and 450 mg of drug/kg of rat, and 0.6 mls of injection vehicle was used for each injection. The injection vehicle consisted of 0.5% w/w sodium carboxy methyl cellulose and 0.1% w/w Tween 80 in water. The microspheres in the suspending media were vortexed at maximum speed for two minutes prior to injection. The injection was performed by locating and injecting slightly below and proximal to the greater trochanter. Rats were anesthetized with halothane 2–3% inspired concentration in oxygen during injections, at least five rats were used to test each formulation.

Testing for Sciatic Nerve Block or Anesthesia Effect

Male Sprague-Dawley Charles River rats weighing between 200 and 350 mg were used to determine the duration of the block obtained with each of the different microsphere formulations tested. They were handled daily and habituated to the testing paradigm prior to exposure to local anesthetic injections. Sensory and motor blockade or anesthesia effect were examined as described above. The duration of the sensory block was determined as the length of time for which the latency was greater than or equal to 7 seconds.

In addition to sensory testing, motor testing was performed at each time point to examine the rat's ability to hop and to place weight on its hind leg. Animals were handled and cared for according to institutional, state, and federal regulation, and according to the guidelines of the International Association for the Study of Pain, Seattle, Wash.

RESULTS

Microsphere morphology

Using the preparative procedures outlined above, smooth, spherical, mechanically stable microspheres were produced without significant quantities of crystalline bupivacaine leaching out the microspheres. When the drug leached out of the microspheres into the aqueous solution, it was in the form of long crystals, approximately 30$\mu$ in length and was visible by light microscopy. Comparison of PLGA microspheres loaded with 75% bupivacaine and 0.05% dexamethasone formulated by solvent removal using a vacuum at 40° C. with those formulated by stirring the microspheres at room temperature and pressure, for three hours until the organic solvent evaporated, showed significant differences. Increasing the rate of removal of the organic solvent using heat and vacuum reduced the rate of leaching of bupivacaine out of the microspheres.

In vitro release kinetics

Figure 7:
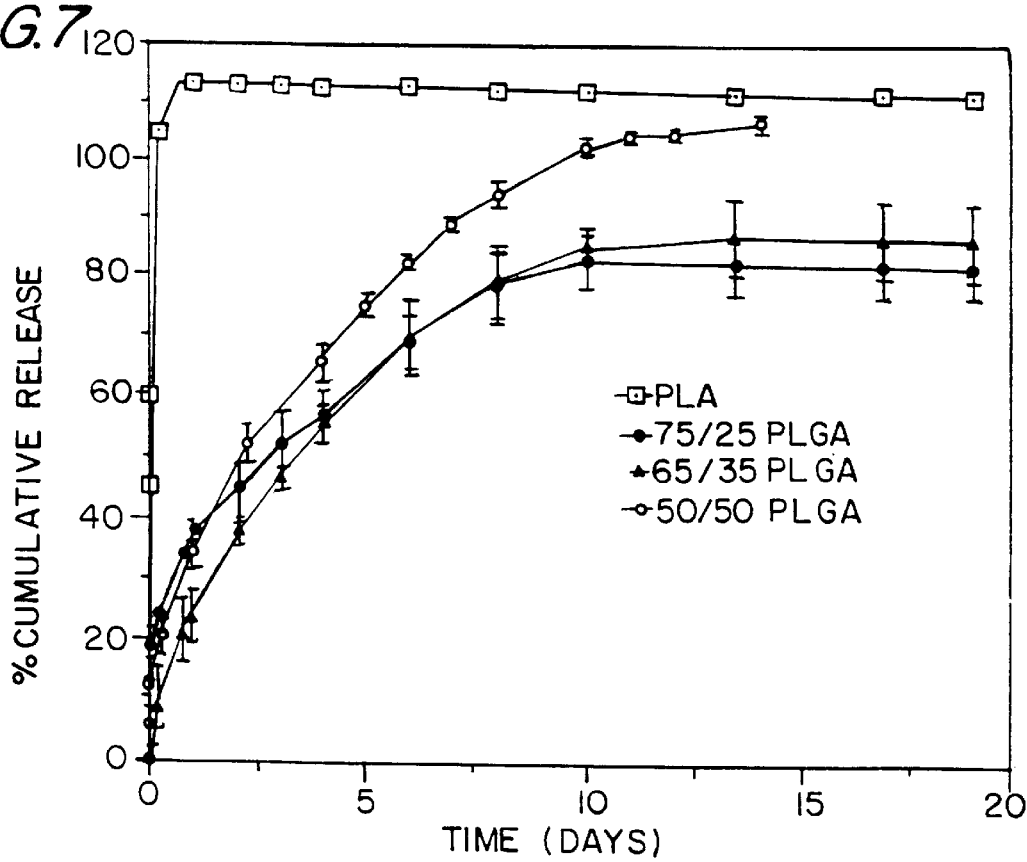
FIG. 7 is graph of the percent cumulative release over time (days) for microspheres containing 75%, bupivacaine, by weight, prepared from PLA 100 (squares), PLGA 75.25 (closed circles), PLGA 65:35 triangles and PLGA 50:50 (circles).

FIG. 7 is a graph of % cumulative release of bupivacaine from PLA and PLGA copolymers, PLGA 50:50, 75:25, and 65:35, over time. The results demonstrate that there is. a burst of release of drug from PLA initially, which is substantially less in the PLGA copolymers.

Other polymers have been tested. Ethyl cellulose and polyhydroxyvalerate-butyrate ("PHBV") microspheres (20 to 140 microns in diameter) containing 50 and 75% by weight bupivacaine, with or without 0.05% dexamethasone, showed different respective release rates. Ethyl cellulose microspheres released 31% bupivacaine during the first day and PHBV microspheres released 70% bupivacaine in during the first day, with efficacy confirmed by in vivo studies.

The similar in vivo latency durations resulting from bupivacaine encapsulated into PLGA 50:50, 65:35, 75:25 PLGA and PLA are shown in FIGS. 4A–4D Comparison of the % cumulative release of bupivacaine from microspheres when the pH of the buffer media was 6, 7.4 and 8 shows that the rate of release of bupivacaine was higher at pH 6 than at pH 7.4 or 8, because bupivacaine has greater water solubility at pH 6 than at pH 7.4 or pH 8 (data not shown).

Radiolabeled Microspheres

When microspheres loaded with unlabeled bupivacaine and radiolabled dexamethasone were prepared, the yield (weight of microspheres/weight of bupivacaine+weight of polymer) was 45%. The bupivacaine content was determined to be 75±1%. When microspheres loaded with unlabeled dexamethasone and radiolabeled bupivacaine were prepared, the yield was 50%, and the bupivacaine content was 73±2%. Comparisons of the percent cumulative release of both tritium labeled dexamethasone and tritium labeled bupivacaine, proves that dexamethasone was incorporated into the microspheres and that both substances were released at similar release rates.

Rat Sciatic Nerve Blockade In Vivo

Figure 2:
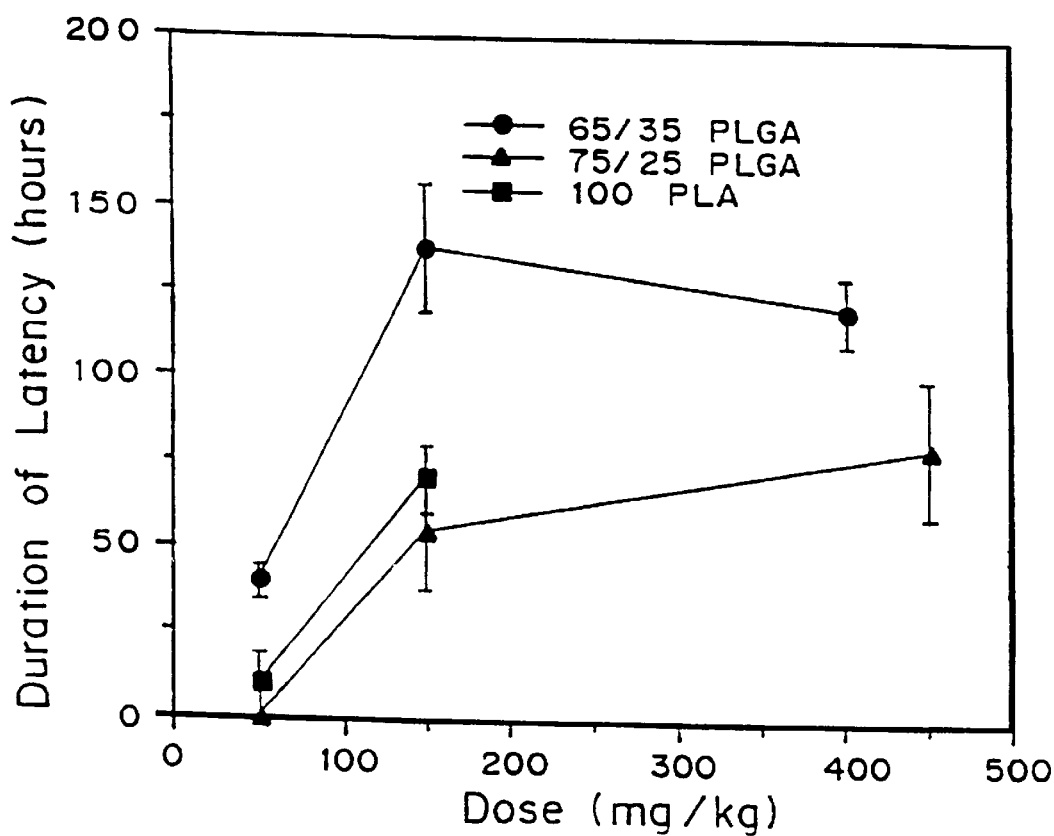
FIG. 2 is a graph of the duration of sensory latency (hours) verses bupivacaine dose, in animals treated with microspheres containing bupivacaine 75% (w/w) and 0.05% dexamethasone prepared from 100 polylactic acid ("PLA"; square), copolymer of lactic and glycolic acid ("PLGA") 65:35 (circle), and PLGA 75:25 (triangle) loaded with bupivacaine and dexamethasone, administered at doses of 50 to 450 mg of bupivacaine/Kg rat. Duration was defined as the mean duration of time for which the for which the latency of a group of 5 rats was greater than or equal to 7 seconds. Error bars indicate standard errors.

In order to determine the toxic response of the rats to various microsphere doses, the rats were injected with concentrations ranging from 50 to 450 mg of bupivacaine/kg of rat for each 100 polylactic acid (PLA), polylactic, polyglycolic acid copolymer ("PLGA") 65:35 and 75:25 (FIG. 2).

No systemic toxicity, excessive sluggishness or death was observed even at the highest doses.

Figure 3A:
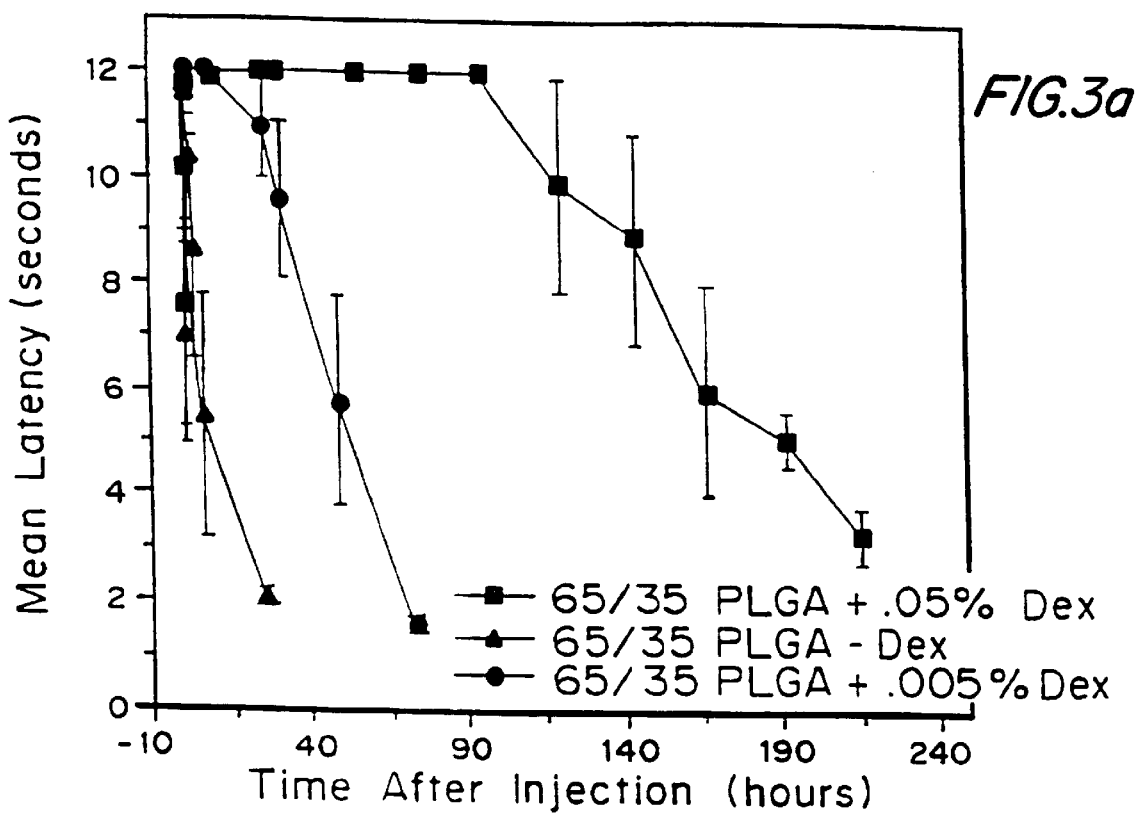
FIG. 3A is a graph of the duration of latency versus time (hours), determined by sensory testing using the modified hot plate test for 75% bupivacaine loaded PLGA 65:35 containing 0.05%, 0.005%, and 0.0% dexamethasone. Error bars indicate standard errors.
Figure 3B:
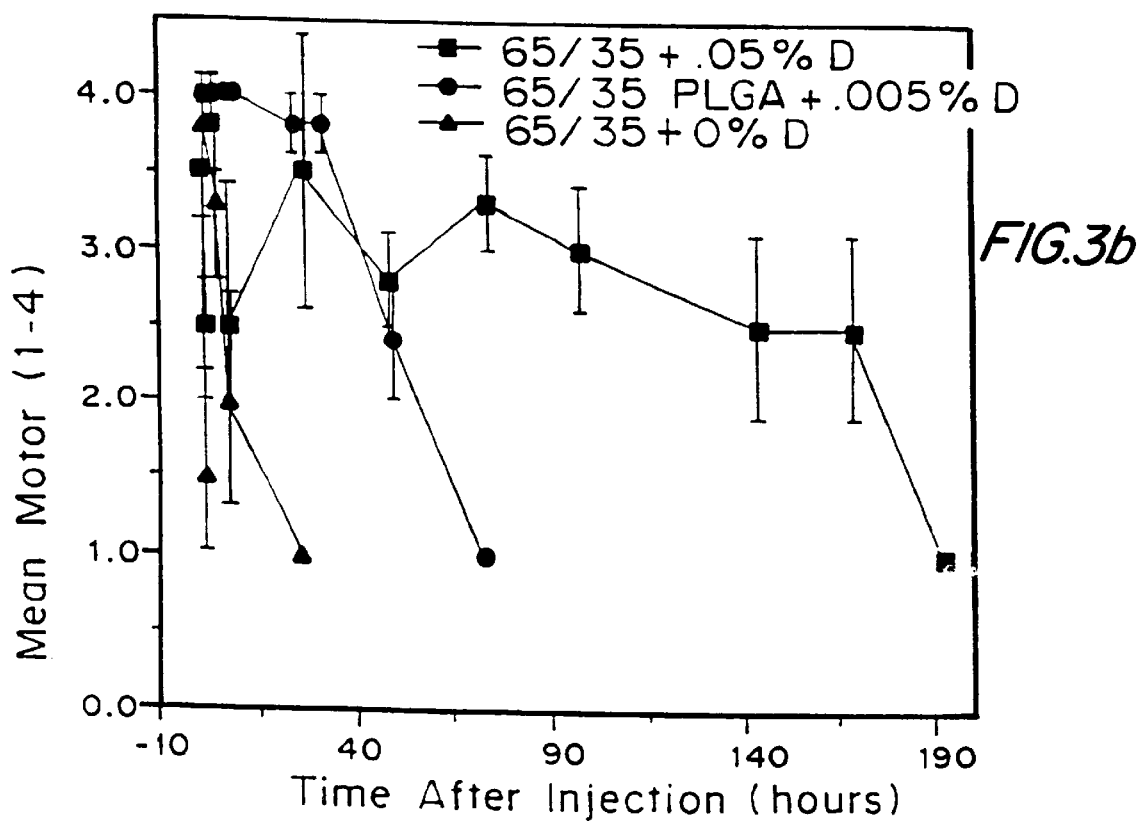
FIG. 3B is a graph of the duration of latency versus time (hours), determined by by motor testing (FIG. 3b) for 75% bupivacaine loaded PLGA 65:35 containing 0.05%, 0.005%, and 0% dexamethasone. Error bars indicate standard errors.
Figure 4A:
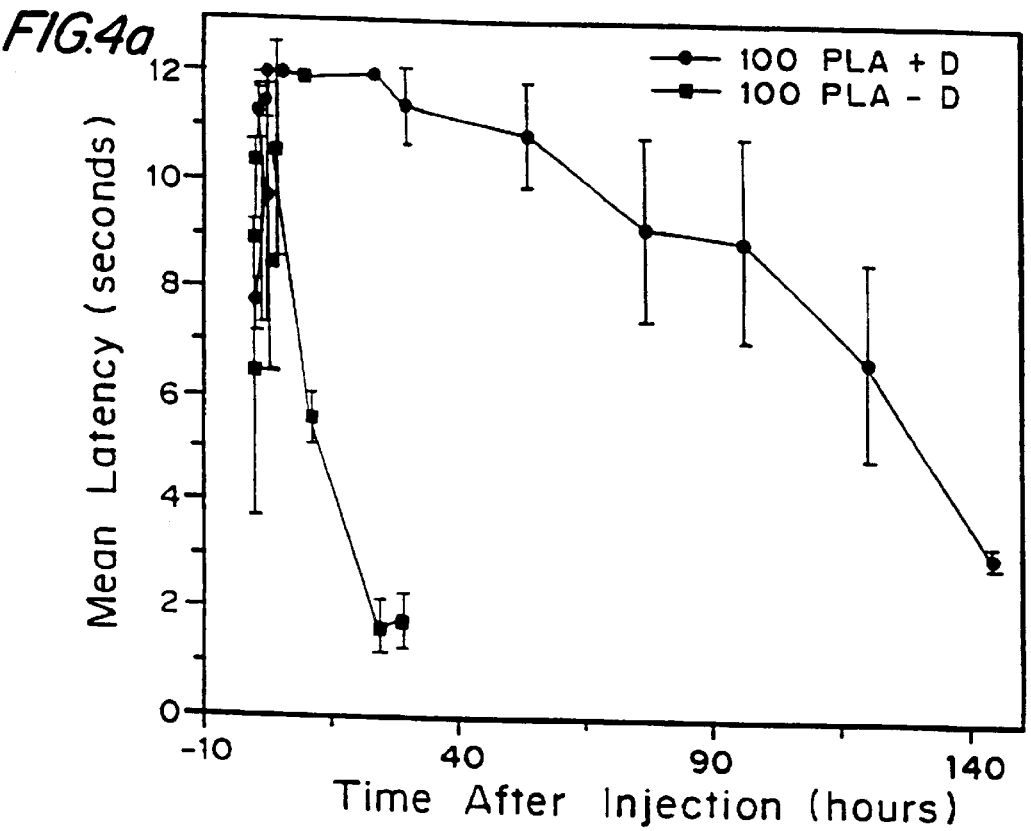
FIG. 4A is a graph comparing the duration of latency (secs) versus time (hours) after injection, determined using the modified hot plate test for 100 PLA microspheres loaded with 75% bupivacaine which contained 0.05% dexamethasone (circles) with corresponding microspheres which did not contain dexamethasone (squares). Error bars indicate standard errors.
Figure 4B:
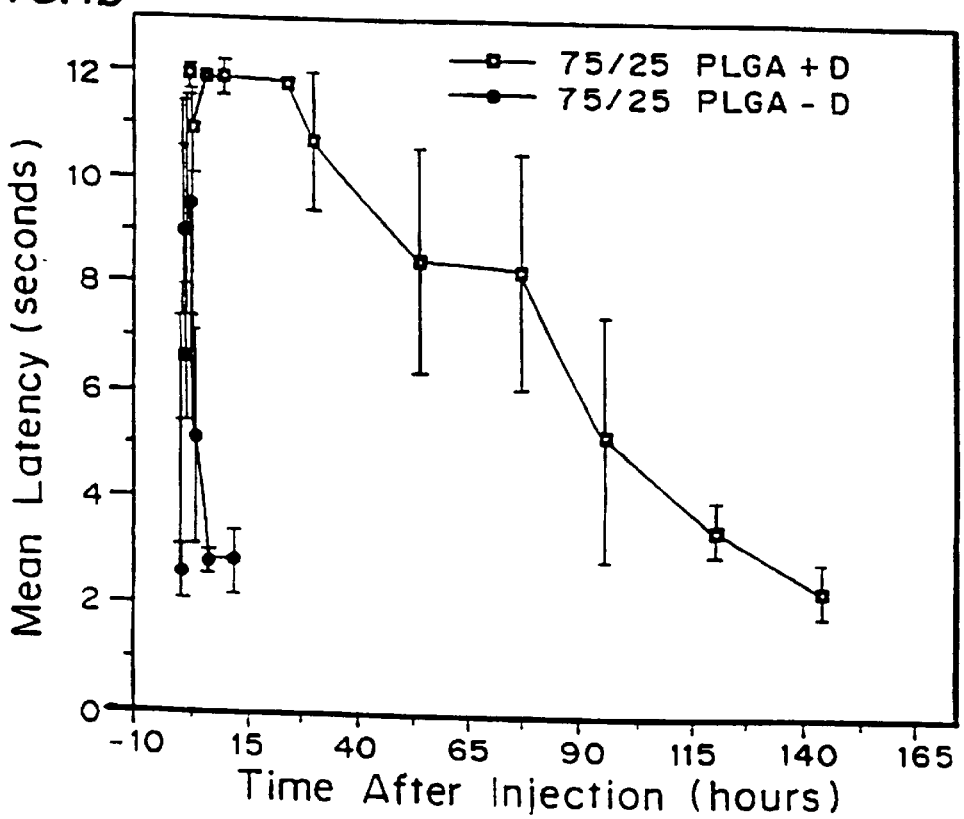
FIG. 4B is a graph comparing the duration of latency (secs) versus time (hours) after injection, determined using the modified hot plate test for PLGA 75:25 microspheres loaded with 75% bupivacaine which contained 0.05% dexamethasone (squares) with corresponding microspheres which did not contain dexamethasone (circles). Error bars indicate standard errors.
Figure 4C:
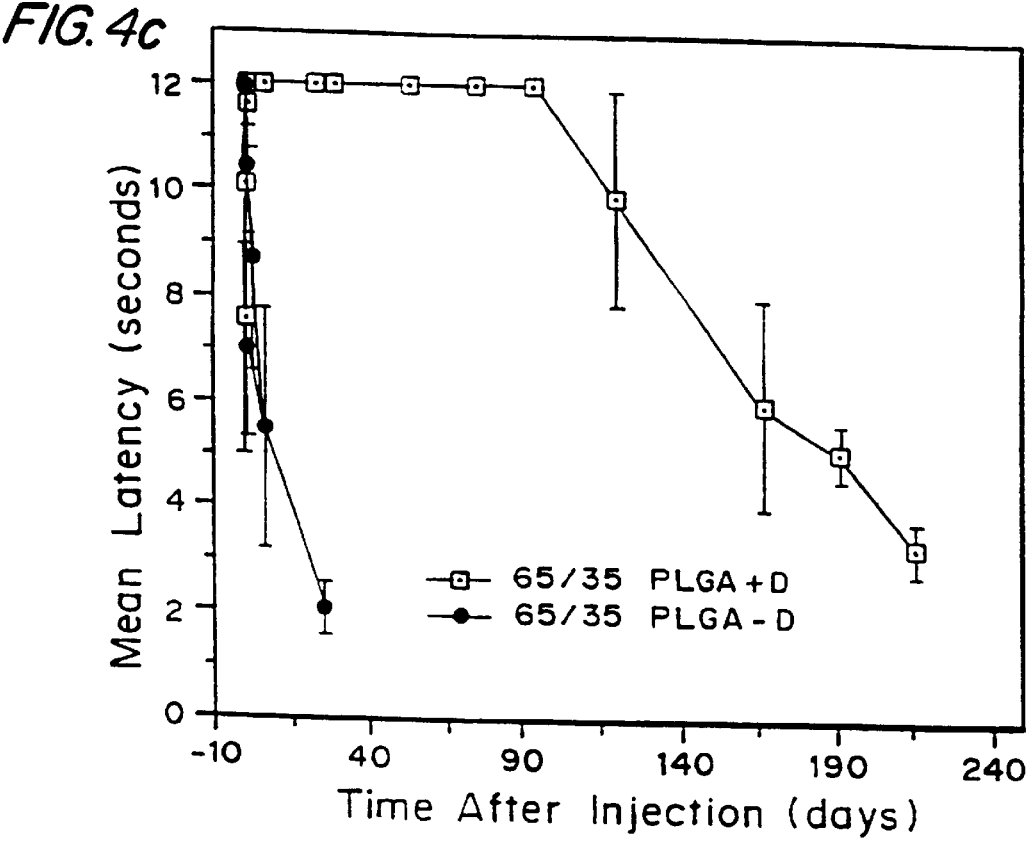
FIG. 4C is a graph comparing the duration of latency (secs) versus time (hours) after injection, determined using the modified hot plate test for 65:35 PLGA microspheres loaded with 75% bupivacaine which contained 0.05% dexamethasone (open squares) with corresponding microspheres which do not contain dexamethasone (closed circles). Error bars indicate standard errors.
Figure 4D:
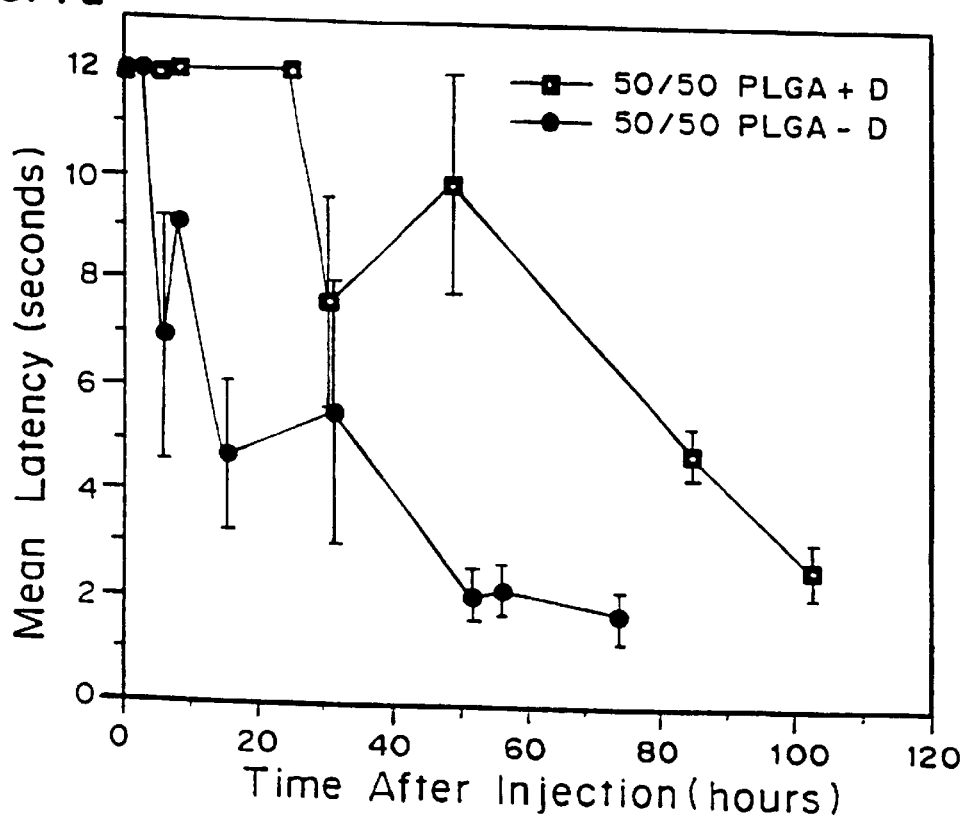
FIG. 4D is a graph comparing the duration of latency (secs) versus time (hours) after injection, determined using the modified hot plate test for 50:50 PLGA microspheres loaded with 75% bupivacaine which contained 0.05% dexamethasone (squares) with corresponding microspheres which do not contain dexamethasone (circles). Error bars indicate standard errors.

A comparison of the latencies and mean motor times obtained from PLGA 65:35 microspheres which contained 0.0%, 0.005% and 0.05% dexamethasone, respectively, at a dose of 150 mg bupivacaine/kg of rat provided nerve block durations of 8, 50 and 170 hours, respectively (FIG. 3A) and decreased motor skills (FIG. 3B) with, respectively. The optimum dose and formulation was determined to be 150 mg of drug/kg of rat of PLGA 65:35 microspheres loaded with 75% bupivacaine and 0.05% dexamethasone, as this was the lowest dose which resulted in the longest duration of block.

Figure 5A:
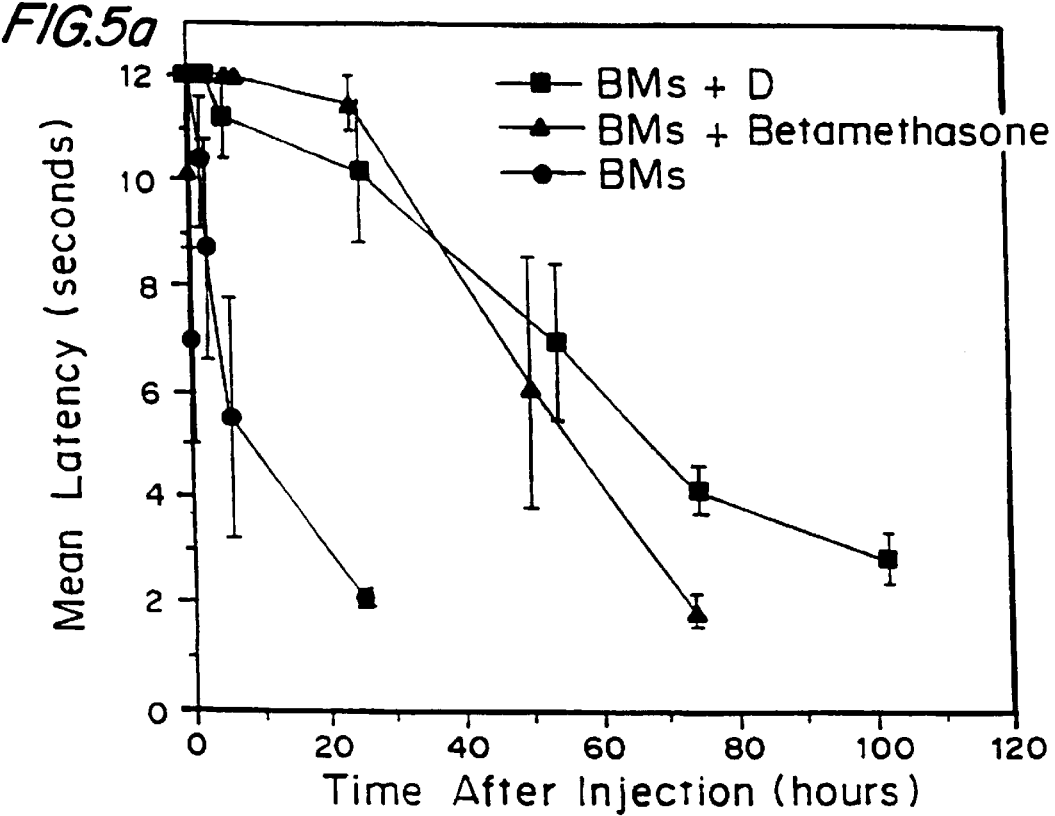
FIGS. 5A is a graph of the duration of sensory block in hours after injection of bupivacaine loaded microspheres (circles), bupivacaine loaded microspheres with dexamethasone in the injection fluid (squares), and bupivacaine loaded microspheres with betamethasone in the injection fluid (triangles).
Figure 5B:
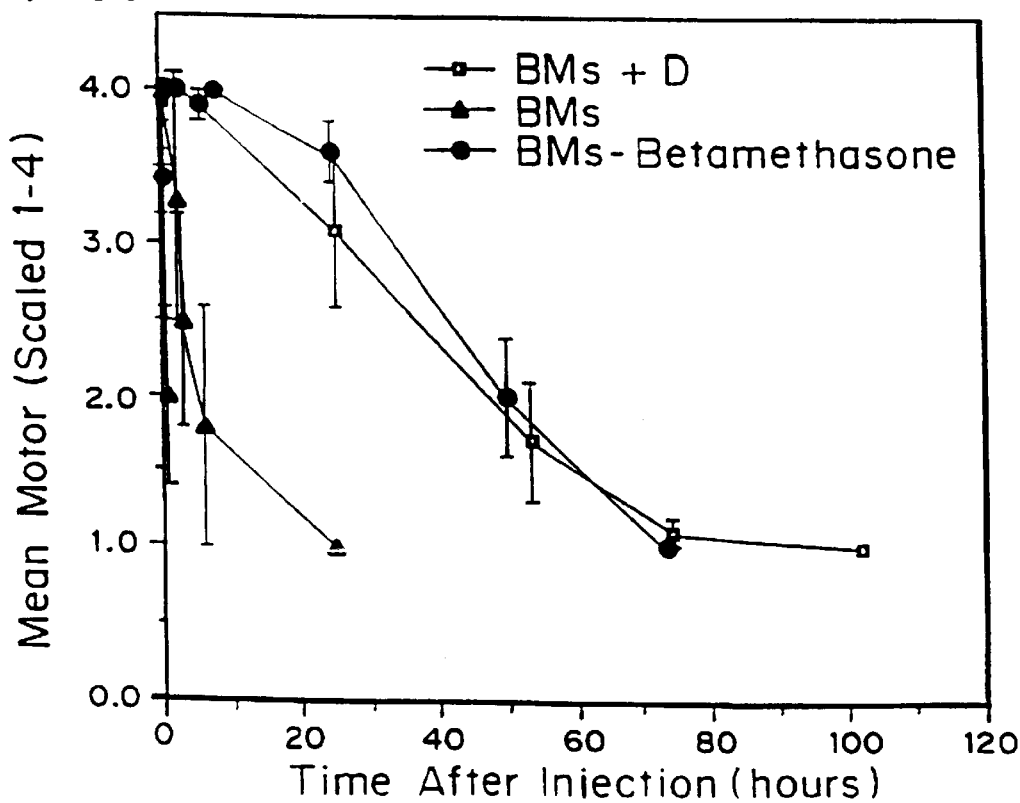
FIG. 5B is a graph of the duration of motor block in hours after injection of bupivacaine loaded microspheres (triangles), bupivacaine loaded microspheres with dexamethasone in the injection fluid (squares), and bupivacaine loaded microspheres with betamethasone in the injection fluid (circles).

The presence of 0.05% dexamethasone or betamethasone in the injection fluid significantly prolonged the duration of sensory (FIG. 5A) and motor (FIG. 5B) sciatic nerve block (FIGS. 5A–5B). Similarly, the presence of dexamethasone, betamethasone, methylprednisolone or hydrocortison in microspheres also significantly prolonged the duration of sciatic nerve block (e.g., see FIG. 6). That is, the block or anesthesia effect obtained using microspheres which contained, e.g., 0.05% dexamethasone was up to 13 fold longer than the block or anesthesia effect obtained using the corresponding microspheres which did not contain any dexamethasone. It was determined that 150 mg of microspheres /Kg of rat was the optimum dosage and produced the greatest prolongation of block.

The duration of sensory block for groups of rats injected with bupivacaine loaded PLA 100, PLGA 75:25, PLGA 65:35 and PLGA 50:50 microspheres, with and without incorporated dexamethasone was compared. In each case, the presence of dexamethasone in the microspheres resulted in a 6–13 fold increase in. the duration of block (see FIGS. 4A–D). Mean sciatic nerve block durations among treatment groups varied from 65±3 to 134±13 hours for microsphere formulations which contained dexamethasone. Control groups receiving injections of polymer microspheres containing no drug or dexamethasone or containing dexamethasone alone showed no sensory or motor block.

The in vitro results showed that the bupivacaine was released from the microspheres in a controlled manner. In general, 24–40% of the bupivacaine was released in the first 24 hours, and approximately 7% released daily thereafter. After 5–8 days approximately 90% of the bupivacaine was released. The presence of dexamethasone in the microspheres did not significantly affect the in vitro release rates of bupivacaine (e.g., see FIG. 1) and the in vitro results cannot account for the prolongation of block, due to the presence of dexamethasone observed in vivo.

Example 2

Animal Testing Procedures

The following methods were utilized in the in vivo studies on rats. The rats were kept at room temperature (e.g., 22–25° C.), unless otherwise indicated.

Nerve Block Tests

Motor Anesthesia

The rats were behaviorally tested for sensory and motor blockade or anesthesia effect in a quiet observation room. Testing was only performed in rats showing appropriate baseline hot plate latencies after at least one week of testing. In all testing conditions, the experimenter recording the behavior was unaware of the side containing the local anesthetic. To assess motor block or anesthesia, a 4-point scale based on visual observation was devised. (1) normal appearance, (2) intact dorsiflexion of foot with an impaired ability to splay toes when elevated by the tail, (3) toes and foot remained plantar flexed with no splaying ability, and (4) loss of dorsiflexion, flexion of toes, and impairment of gait. For graphing clarity, partial motor block equals a score of 2 and dense motor block is a score of either 3 or 4.

Sensory Anesthesia

Sensory blockade or anesthesia effect was measured by the time required for each rat to withdraw its hind paw from a 56° C. plate (IITC Life Science Instruments, Model 35-D, Woodland Hills, Calif.). They were tested daily at standard room temperature and allowed to adjust to their surroundings in a quiet room for at least 30 minutes before testing, also at room temperature. The rats were held with a cloth gently wrapped above their waist to restrain the upper extremities and obstruct vision. The rats were positioned to stand with one hind paw on a hot plate and the other on a room temperature plate. With a computer data collection system (Apple IIe with a footpad switch), latency to withdraw each hind paw to the hot plate was recorded by alternating paws and allowing at least fifteen seconds of recovery between each measurement. If no withdrawal occurred from the hot plate within 12 seconds, the trial was terminated to prevent injury and the termination time was recorded. Testing ended after five measurements per side, the high and low points were disregarded, and the mean of the remaining three points was calculated for each side. Animals were handled in accordance with institutional, state and federal guidelines.

No rats were observed to have inflammation or blisters (data from formlation in the form of surgically implanted pellets). Rats were tested for at least two weeks prior to surgery to insert the implants to achieve a consistent baseline latency, and testing continued for two weeks after surgery to confirm complete recovery from sensory blockade or anesthesia effect. Motor blockade or anesthesia effect was rated on a 4-point scale. Animals with a motor block or anesthesia effect 4 had a clubbed hindpaw and usually dragged their affected leg when walking. Motor block or anesthesia effect 3 animals walked normally but had toes that failed to splay when the animal was lifted. Animals with motor block or anesthesia effect of 2 showed toes that splayed but not as fully as normal or motor block or anesthesia effect 1 animals.

Necropsy and Histology

Animals were sacrificed two weeks after implantation. Sections of sciatic nerve approximately 2–3 cm in length, adjacent and proximal to the implants, were preserved in 10% formalin solution (24 mM sodium phosphate, pH 7). Sections were then embedded in paraffin, stained with hematoxylin and eosin, and examined by light microscopy.

Plasma Analysis

Rats (250–275 g) anesthetized with ketamine-HCl (100 mg/ml at 1.5 ml/kg, i.p.) and xylazine (4 mg/ml at 4 mg/kg, i.p.), were implanted with a silastic catheter into the right jugular vein. Blood was withdrawn (0.5 cc) before implantation and at timed intervals after administration via the indwelling central venous cannulae. Plasma was extracted with an equal volume of HPLC grade methanol (Fischer Scientific, Pittsburgh, Pa.), centriftiged (10,000×g) and the methanol phase filtered (0.2 $\mu$m nylon syringe type, Rainin, Woburn, Mass.) prior to HPLC analysis. The HPLC reliably quantified bupivacaine concentrations in the plasma methanol extraction phase down to 10 ng/ml. The bupivacaine standards used for blood plasma analyses were added to plasma aliquots prior to methanol extraction. The peak matching the standard bupivacaine peak's retention time was verified in plasma samples by doping with bupivacaine.

Statistics

Data were analyzed using linear regression tests, ANOVA, Chi Square tests and Wilcoxon rank-sum tests, where appropriate.

Example 3
Administration of Microspheres in combination with Glucocorticoids in solution Example 1 demonstrated that incorporation of 0.05% dexamethasone into either pellets or microspheres resulted in prolongation of block from 50–60 hours when microspheres which contained 0.05% dexamethasone were used versus 6–10 hours in the case of microspheres which contained no dexamethasone. To further understand the mechanism, a model system was developed whereby different additives: steroids, steroidal anti-inflammatories, and non-steroidal anti-inflammatories (NSAIDs), were placed in the injection fluid to determine if the block could be prolonged and to screen for block prolonging activity. In this model system, the additives were placed into the injection fluid immediately prior to injection, and the microspheres used contained bupivacaine, but no dexamethasone. If the additive was a solid, it was dissolved in ethanol and aliquots of concentrations which varied between 0.005 and. 5% (weight of additive/weight of microspheres). If the additive was in liquid form, then the amount was added directly to the injection fluid.

The results demonstrated that the duration of sciatic blockade or anesthesia effect from bupivacaine-polyester microspheres was prolonged by incorporation of glucocorticoid into the microspheres, which is proportional to the strength of the glucocorticoid in the injection fluid.

Materials and Methods

Formulation of PLGA Microspheres and Protocol for In Vitro Release Studies
Formulation of Microspheres of 65:35 loaded with 75% bupivacaine with 0.05% dexamethasone 50 mg of PLGA 65:35 (High molecular weight) and 150 mg of bupivacaine free base (obtained from Perdue-Frederick) were dissolved in 0.1 ml of a solution of 5 mg of dexamethasone in 5 mls in $CH_2CL_2$ and 0.9 mls of $CH_2CL_2$. 1 ml of 0.3% polyvinyl alcohol (PVA) in 100 mM Tris buffer at. pH 8.5 was added. and the mixture vortexed 3 times for 15 seconds each time. The mixture was poured into 100 mls of 0.1% PVA in 100 mM Tris buffer. The microspheres were examined using the light microscope and the size distribution was determined, using a coulter counter, to be between 10 and 110 microns. The $CH_2Cl_2$ was removed by heating the sample to 31° C. using a rotary evaporator at full vacuum for 15 minutes. The suspension of microspheres in 0.1% PVA was filtered through 140, 60, and 20$\mu$ metal sleeves (Newark Wire Cloth Co.). Then the microspheres were frozen in liquid nitrogen and lyophilized overnight.
Formulation of Microspheres which contained tritium labeled dexamethasone Radiolabeled dexamethasone was purchased from Amersham and an aliquot which contained 200,000 counts was added to cold dexamethasone and the microspheres were formulated as above.
Formulation of Microspheres which contained tritium labeled Bupivacaine Radiolabeled bupivacaine was kindly donated by Dr. Gary Strichartz from Brigham and Woman's Hospital. Again the bupivacaine was dissolved in ethanol and an aliquot which contained 200,000 counts was added to cold bupivacaine and the microspheres were formulated as above.

Analysis of the in vitro release of either tritium labeled dexamethasone or bupivacaine The in vitro release studies were carried out as outlined above except that instead of monitoring the release by U.V. spectroscopy, the in vitro release was determined by adding 15 mls of Ecolume™ to each 2 ml aliquot of buffer, and the subsequent disintegrations were monitored using a scintillation counter.

Preparation of the Suspension

A ratio of 150 mg bupivacaine/kg was injected. The corresponding amount of microspheres is 200 mg/kg. The microspheres are weighed out and transferred to a 3 cc syringe via the plunger. The needle of the syringe is removed and the opening covered with Parafilmm. Carboxymethylcellulose sterilized by filtration through a 0.2 micron filter is used as the injection fluid.

The rats are tested at 0.5, 1, 2, 3, 6, 8 and 24 hours after injection and then once daily until the block wears off. The rat is motor and sensory tested each time as described above using a hotplate at 56° C.

Results

Table 1 summarizes the results of these experiments.

TABLE 1

| Number of rats | Additives (mg/Kg rat) | Sensory block (hours) | Motor block (hours) |
|---|---|---|---|
| 11 | — | 6.0 ± 1.0 | 5.0 ± 0.3 |
| 7 | Dexamethasone (0.14) | 47.0 ± 8.0 | 38.0 ± 5.0 |
| 5 | Dexamethasone (0.02) | 17.0 ± 11.0 | 19.0 ± 8.0 |
| 5 | Dexamethasone (2.0) | 36.0 ± 19.0 | 34.0 ± 12.0 |
| 5 | Betamethasone (2.0) | 44.0 ± 13.0 | 39.0 ± 11.0 |
| 5 | Betamethasone (0.8) | 46.0 ± 7.0 | 39.0 ± 5.0 |
| 5 | Betamethasone (0.25) | 36.0 ± 10.0 | 38.0 ± 11.0 |
| 5 | Betamethasone (0.032) | 19.0 ± 4.0 | 15.0 ± 4.0 |
| 5 | Methylprednisolone (20) | 34.0 ± 11.0 | 33.0 ± 9.0 |
| 7 | Methylprednisolone (2.1) | 28.0 ± 6.0 | 28.0 ± 5.0 |
| 5 | Methylprednisolone (0.1) | 20.0 ± 5.0 | 13.0 ± 4.0 |
| 7 | Hydrocortisone (0.1) | 10.0 ± 3.0 | 10.0 ± 3.0 |
| 5 | Hydrocortisone (1.25) | 15.0 ± 5.0 | 16.0 ± 3.0 |
| 5 | Hydrocortisone (10) | 36.0 ± 10.0 | 31.0 ± 8.0 |
| 5 | Ketoralac (2.0) | 6.0 ± 0.7 | 7.0 ± 0.4 |
| 5 | Ketoralac (6.3) | 8.0 ± 2.0 | 10.0 ± 4.0 |
| 4 | Estradiol (1.25) | 8.0 ± 1.0 | 9.0 ± 2.0 |
| 4 | Estradiol (0.125) | 11.0 ± 6.0 | 12.0 ± 6.0 |
| 8 | Cholesterol (0.1) | 4.0 ± 0.4 | 4.0 ± 1.0 |
| 5 | Cholesterol (3.1) | 8.0 ± 3.0 | 5.0 ± 1.0 |
| 5 | Testosterone (1.7) | 15.0 ± 5.0 | 15.0 ± 5.0 |
| 5 | Testosterone (1.0) | 7.0 ± 2.0 | 6.0 ± 1.0 |
| 4 | Progesterone (2.0) | 8.0 ± 1.0 | 6.0 ± 1.0 |
| 5 | Epinephrine (0.01) | 12.0 ± 6.0 | 12.0 ± 4.0 |
| 5 | Epinephrine (0.1) | 14.0 ± 5.0 | 11.0 ± 3.0 |

The results demonstrate that dexamethasone does not produce sciatic blockade or anesthesia effect by itself in solution, nor does it prolong blockade or anesthesia effect from bupivacaine in solution. Addition of dexamethasone in solution with bupivacaine in solution did not prolong blockade or anesthesia effect relative to bupivacaine in solution alone. The prolonged blockade or anesthesia effect previously observed seemed to require the presence of bupivacaine in microspheres.

A model system was developed in which dexamethasone was dissolved in ethanol and an aliquot of known concentration was added to the suspending medium which contained microspheres loaded with 75% bupivacaine. Addition of dexamethasone to the suspending medium in concentrations ranging from 0.05% to 0.5% prolonged the duration of blockade or anesthesia effect obtained using bupivacaine microspheres, Addition of 0.005% w/w bupivacaine did not result in a prolongation of the blockade or anesthesia effect obtained. The result of this model system was useful, because it permitted testing of a series of compounds over full concentration ranges for prolongation of sciatic block in vivo without the labor-intensive step of making a microsphere prep with each additive and each dose.

Studies were conducted to determine whether dexamethasone's prolongation of blockade or anesthesia effect is unique, or whether it can be replicated by: (1) other glucocorticoids, (2) other classes of steroids, or (3) other drugs with anti-inflammatory activity, including non-steroidals (NSAIDs). For example, it is well known that cholesterol and other steroids modify membrane lipid phase equilibria, and it is conceivable that effects on lipid physical state could perturb sodium channel function and amplify or prolong channel blockade from local anesthetics. The question was also raised as to whether the dexamethasone effect was due to changes in regional perfusion, analogous to epinephrine's effect.

Figure 6:
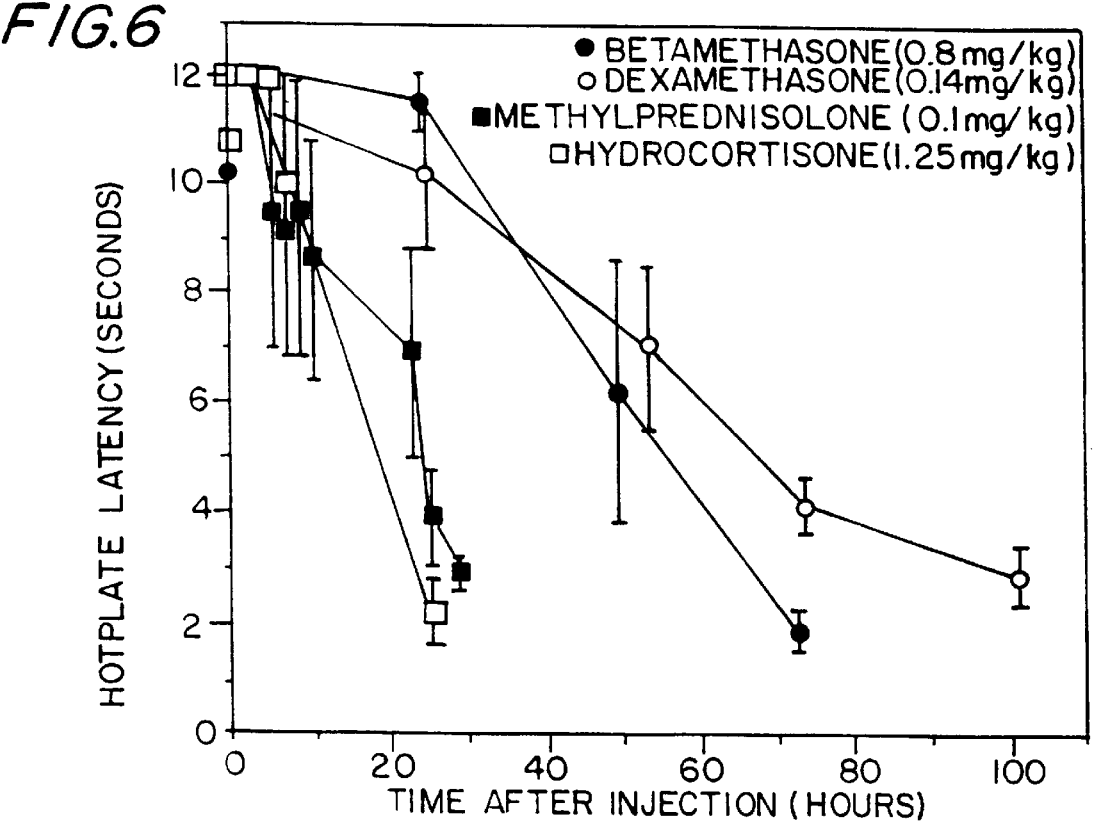
FIG. 6 is a graph of sensory block over time after injection (hours) in rats of PLGA 65:35 microspheres containing bupivacaine and with one of four glucocorticoids in the injection fluid: betamethasone (0.8 mg/kg), dexamethasone (0.14 mg/kg), methylprednisolone (0.1 mg/kg), and hydrocortisone (1.25 mg/kg) in the injection fluid.

FIG. 6 compares the effect of various glucocorticoids on duration of nerve blockade or anesthesia effect when administered in combination with microspheres having bupivacaine incorporated therein. The data confirm that glucocorticoids prolong nerve block in proportion to their potency as glucocorticoids. It can be seen that:

1. High potency glucocorticoids such as betamethasone also produce prolongation of anesthesia up to 45 hours in duration.
2. Intermediate potency glucocorticoids such as methylprednisolone produce intermediate degrees of anesthetic prolongation.
3. Weaker glucocorticoids such as hydrocortisone produce mild, but statistically significant prolongation of anesthesia.
4. The weaker prolongation of block by hydrocortisone cannot be made as effective as dexamethasone by further increasing its concentration in the suspending medium.
5. Estradiols showed little if any significant anesthesia-prolonging effect under these conditions. Testosterone indicated a modest prolongation of anesthesia.
6. NSAIDs and epinephrine did not substantially prolong blockade or anesthesia effect, Epinephrine in the doses used (0.05% in the suspending medium) produced considerable systemic toxicity, but no deaths.

Preliminary reports on the histologic effects are that they are benign, with no evidence of major axonal or demyelinating injury and only mild inflammation.

A long duration of block was produced using 150 mg/kg rat body weight with 75% bupivacaine loaded PLGA 65:35 microspheres. Doses as high as 600 mg/kg can be given with temporary somnolence as a side-effect, but no convulsions or cardiac arrests.

The dosing of dexamethasone in the microspheres (0.05%) is quite low, particularly considering its delayed release. Even when this concentration of dexamethasone was added in the suspending medium (permitting immediate access for absorption), no systemic effects were found. In one experiment using dexamethasone 0.5% in the suspending medium, no immediate toxicities occurred, but among five rats there were two deaths at 12–15 days post injection, and at the same time a third rat appeared thin and pale.

Experiments confirmed that 65:35 PLGA polymers were preferable to either 75:25 PLGA or 100% PLA, both in terms of (1) the reliability, intensity and duration of sciatic nerve block, (2) each of dispersal and injectability. A blockade or anesthesia effect of 30–40 hours was observed with PLGA 50:50 over the PLGA 65:35 microspheres, indicating no advantage.

Example 4

The combination of local anesthetic in microspheres with glucocorticoid is not a result of altered release rates in vivo Additional studies were conducted as described above to further elucidate the mechanisms involved in the prolongation of the nerve blockade or anesthesia effect by the glucocorticoid. In this study, bupivacaine (measured in mg) remaining in. microspheres that were extracted from rats as a function of time in days following injection was determined (data not shown). The study compared the amount of bupivacaine released as a function of polymer, comparing PLGA 75:25 with and without dexamethasone, PLGA 65:35 with and without dexamethasone, PLGA 50:50 with and without dexamethasone, and PLA containing bupivacaine and dexamethasone. The results demonstrate that the drug is being released over time as expected, and that release is not altered by the presence or absence of dexamethasone. Accordingly, while not wishing to be bound by any hypothesis as to how this occurs, the glucocorticoid may be exerting an effect directly on the nerve, not by interaction with the local anesthetic.

The examples provided above are not meant to be exclusive. Many other variations of the present invention would be obvious to those skilled in the art, and are contemplated to be within the scope of the appended claims. Numerous publications are cited herein, the disclosures of which are incorporated herein by reference in their entireties.

What is claimed is:

1. A formulation for providing pain relief at a site in a patient comprising a local anesthetic in a biocompatible biodegradable controlled release form and a glucocorticosteroid in an amount effective to prolong the effect of the local anesthetic such that the duration of effect is greater than that obtained by use of the same dose of local anesthetic in controlled release form in the absence of the glucocorticosteroid.

2. The formulation of claim 1 wherein the controlled release form comprises a biocompatible polymer.

3. The formulation of claim 1 wherein at least a portion of the glucocorticosteroid is incorporated into a separate controlled release form.

4. The formulation of claim 2 wherein the polymer is selected the group consisting of polyanhydrides, copolymers of lactic acid and glycolic acid, polyorthoesters, proteins, and polysaccharides.

5. The formulation of claim 2 wherein the polymer is a copolymer of lactic acid and glycolic acid.

6. The formulation of claim 5 wherein the copolymer comprises a ratio of lactic acid and glycolic acid ranging from about 75:25 to about 50:50 by weight.

7. The formulation of claim 1 wherein the glucocorticosteroid is selected from the group consisting of dexamethasone, cortisone, prednisone, hydrocortisone, beclomethasone dipropionate, betamethasone, flunisolide, methylprednisone, paramethasone, prednisolone, triamcinolone, alclometasone, amcinonide, clobetasol, fludrocortisone, diflorasone diacetate, fluocinolone acetonide, fluocinonide, fluorometholone, flurandrenolide, halcinonide, medrysone and mometasone and pharmaceutically acceptable mixtures and salts thereof.

8. The formulation of claim 1 wherein the glucocorticosteroid is incorporated at a loading between about 0.001 and about 30 percent by weight.

9. The formulation of claim 1 wherein the glucocorticosteroid is dexamethasone.

10. The formulation of claim 1 wherein the local anesthetic is in free base form.

11. The formulation of claim 1 wherein the local anesthetic is selected from the group consisting of bupivacaine, ropivacaine, dibucaine, procaine, chloroprocaine, prilocaine, mepivacaine, etidocaine, tetracaine, lidocaine, and xylocaine, and mixtures thereof.

12. The formulation of claim 1 wherein the local anesthetic is incorporated into the controlled release form at a percent loading of ranging from about 60% to about 85% by weight.

13. The formulation of claim 1 which is in the form selected from the group consisting of slabs, beads, pellets, microparticles, microspheres, microcapsules, and pastes.

14. The formulation of claim 13 which comprises a plurality of microparticles.

15. The formulation of claim 14, which comprises microspheres. suspended in a pharmaceutically acceptable carrier for administration by a method selected from the group consisting of injection, infiltration, infusion or topical application.

16. The formulation of claim 15 wherein at least a portion of the glucocorticosteroid is present in said pharmaceutically acceptable vehicle for injection.

17. The formulation of claim 15 further comprising an outer coating wherein the outer coating flier comprises a pharmaceutically active agent for immediate release selected from the group consisting of a glucocorticosteroid and a local anesthetic and mixtures thereof.

18. The formulation of claim 1 wherein the local anesthesia is effective from about 0.1 hour to about 200 hours after administration.

19. The formulation of claim 1 wherein the local anesthesia is effective from about 1 hour to about 150 hours after administration.

20. A formulation for sustained release of a local anesthetic at a site in a patient comprising a local anesthetic and a glucocorticosteroid incorporated into a biocompatible biodegradable polymer, the formulation including the local anesthetic in a concentration effective to provide pain relief at the site and the glucocorticosteroid in a concentration effective to prolong the effect of the local anesthetic such that the duration of effect is greater than that obtained by use of the same dose of local anesthetic in controlled release form in the absence of the glucocorticosteroid.

21. A method for providing pain relief at a site in a patient, comprising administering a local anesthetic in a controlled release form and administering a glucocorticosteroid at the site in an amount effective to substantially prolong the effect of the local anesthetic such that the duration of effect is greater than that obtained by use of the same dose of local anesthetic in controlled release form in the absence of the glucocorticosteroid.

22. The method of claim 21 wherein the controlled release form comprises a biocompatible polymer.

23. The method of claim 22 wherein the polymer is selected from the group consisting of polyanhydrides, copolymers of lactic acid and glycolic acid, polyorthoesters, proteins, and polysaccharides.

24. The method of claim 21 wherein at least a portion of the glucocorticosteroid is incorporated into a separate biocompatible polymer from the local anesthetic.

25. The method of claim 21 wherein the glucocorticosteroid is selected from the group consisting of dexamethasone, cortisone, prednisone, hydrocortisone, beclomethasone dipropionate, betamethasone, flunisolide, methylprednisone, paramethasone, prednisolone, triamcinolone, alclometasone, amcinonide, clobetasol, fludrocortisone, diflorasone diacetate, fluocinolone acetonide, fluocinonide, fluorometholone, flurandrenolide, halcinonide, medrysone and mometasone and pharmaceutically acceptable mixtures and salts thereof.

26. The method of claim 21 wherein the glucocorticosteroid is dexamethasone.

27. The method of claim 21 wherein the local anesthetic is in free base form.

28. The method of claim 21 wherein; the local anesthetic is selected from the group consisting of bupivacaine, ropivacaine, dibucaine, procaine, chloroprocaine, prilocaine, mepivacaine, etidocaine, tetracaine, lidocaine, and xylocaine, and mixtures thereof.

29. The method of claim 21 wherein the anesthetic is incorporated into the polymer at a percent loading ranging from about 60 percent to about 90 percent by weight.

30. The method of claim 21 wherein the formulation is in the form selected from the group consisting of slabs, beads, pellets, microparticles, microspheres, microcapsules, and pastes.

31. The method of claim 30 wherein the formulation comprises a plurality of microparticles.

32. A formulation for sustained release of a local anesthetic according to claim 1, wherein the controlled release form comprises microcapsules comprising the local anesthetic, the glucocorticosteroid, and a biocompatible, biodegradable polymer, wherein the local anesthetic is present in said microcapsules at a weight percent ranging from about 70 to about 90%.

33. A formulation for providing prolonged pain relief at a site in a patient comprising a local anesthetic incorporated into a biocompatible, biodegradable controlled release form selected from the group consisting of slabs, beads, pellets, microparticles, microspheres, microcapsules, and pastes, said local anesthetic being contained in said controlled release form at a percent loading ranging from about 60 percent to about 90 percent by weight, said controlled release form further comprising a glucocorticosteroid in an amount effective to prolong the effect of local anesthetic such that the duration of effect is greater than that obtained by use of the same dose of local anesthetic in controlled release form in the absence of the glucocorticosteroid.

34. The formulation of claim 33 which comprises microcapsules.

35. The formulation of claim 34, which comprises microcapsules or microspheres suspended in a pharmaceutically acceptable carrier for administration by a method selected from the group consisting of injection, infiltration, infusion or topical application.

36. The formulation of claim 33 wherein the biocompatible, biodegradable controlled release form comprises a polymer selected from the group consisting of polyanhydrides, copolymers of lactic acid and glycolic acid, polyorthoesters, proteins, and polysaccharides.

37. The formulation of claim 36, wherein the biocompatible, biodegradable controlled release form comprises a copolymer of lactic acid and glycolic acid.

38. The formulation of claim 37, wherein the copolymer comprises a ratio of lactic acid and glycolic acid ranging from about 75:25 to about 50:50 by weight.

* * * * *